(12) United States Patent
Hoyt

(10) Patent No.: US 10,107,725 B2
(45) Date of Patent: *Oct. 23, 2018

(54) MULTI-SPECTRAL IMAGING INCLUDING AT LEAST ONE COMMON STAIN

(75) Inventor: Clifford C. Hoyt, Wellesley, MA (US)

(73) Assignee: Cambridge Research & Instrumentation, Inc., Hopkinton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,109

(22) Filed: Jan. 30, 2012

(65) Prior Publication Data

US 2012/0129213 A1    May 24, 2012

Related U.S. Application Data

(63) Continuation of application No. 12/564,857, filed on Sep. 22, 2009, now Pat. No. 8,280,134.

(60) Provisional application No. 61/099,150, filed on Sep. 22, 2008.

(51) Int. Cl.
   *G01N 1/31*      (2006.01)
   *G01N 1/30*      (2006.01)
   *G06K 9/00*      (2006.01)

(52) U.S. Cl.
   CPC ............. *G01N 1/31* (2013.01); *G01N 1/30* (2013.01); *G06K 9/00147* (2013.01)

(58) Field of Classification Search
   None
   See application file for complete search history.

(56) References Cited

U.S. PATENT DOCUMENTS

| | | | |
|---|---|---|---|
| 6,225,636 B1* | 5/2001 | Ginestet | 250/458.1 |
| 6,337,472 B1* | 1/2002 | Garner et al. | 250/201.3 |
| 7,555,155 B2* | 6/2009 | Levenson et al. | 382/133 |
| 7,953,264 B2* | 5/2011 | Levenson et al. | 382/128 |
| 2003/0026762 A1 | 2/2003 | Malmros et al. | |
| 2003/0164819 A1* | 9/2003 | Waibel | 345/173 |
| 2003/0170898 A1* | 9/2003 | Gundersen et al. | 435/461 |
| 2005/0136549 A1* | 6/2005 | Gholap et al. | 436/501 |
| 2007/0098252 A1* | 5/2007 | Cotman et al. | 382/159 |
| 2008/0135490 A1 | 6/2008 | Li et al. | |
| 2008/0294032 A1 | 11/2008 | Levenson et al. | |
| 2010/0069255 A1* | 3/2010 | Borlak et al. | 506/9 |

OTHER PUBLICATIONS

DeCyder 2D Software User Manual, Version 6.5, 28-4010-06 AB, GE Healthcare Bio-Sciences AB, Uppsala, Sweden, Copyright 2005.
Tokutomi et al. (BBRC 364 (2007) p. 822-830).

(Continued)

*Primary Examiner* — Melanie Yu Brown
*Assistant Examiner* — Richard Moerschell
(74) *Attorney, Agent, or Firm* — Fish & Richardson P.C.

(57) ABSTRACT

A method including: providing a sample with M components to be labeled, where M>2; labeling the components with N stains, where N<M so that at least two components are labeled with a common stain; obtaining a set of spectral images of the sample; classifying different parts of the sample into respective classes that distinguish the commonly stained components based on the set of spectral images; and determining relative amounts of multiple ones of the M components in different regions of the sample. Related apparatus are also disclosed.

8 Claims, 17 Drawing Sheets

(56) References Cited

OTHER PUBLICATIONS

Bala et al., "Hybrid Learning Using Genetic Algorithms and Decision Trees for Pattern Classification," IJCAI 1: 719-724 (1995).
R. Poli, "Genetic Programming for Image Analysis," Proceedings of the 1st Annual Conference on Genetic Programming, MIT Press (1996), pp. 363-368.
C. Burges, "A Tutorial on Support Vector Machines for Pattern Recognition," *Data Mining and Knowledge Discovery* 2: 121-167 (1998).
Suykens et al., "Least Squares Support Vector Machine Classifiers", Neural Processing Letters 9(3): 293-300 (1999).
Furey et al., "Support vector machine classification and validation of cancer tissue samples using microarray expression data," *Bioinformatics* 16(10): 906-914 (2000).
Perkins et al., "Genie: A Hybrid Genetic Algorithm for Feature Classification in Multi-Spectral Images," Proc. SPIE 4120: 52 (2000).
Tsai et al., "Medical image classification using genetic-algorithm based fuzzy-logic approach," *J. Electronic Imaging* 13(4): 780-788 (2004).
Chen et al., "A Tutorial on υ-Support Vector Machines", *Applied Stochastic Models in Business and Industry* 21(2): 111-136 (2005).

\* cited by examiner

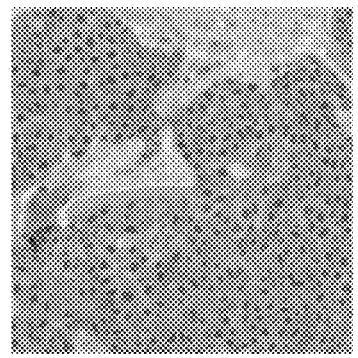
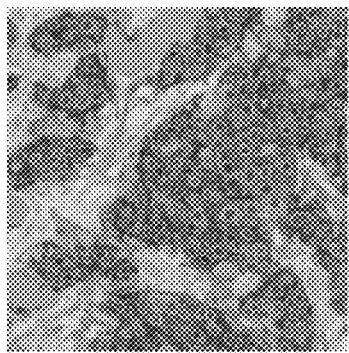
FIGURE 14A  FIGURE 14B
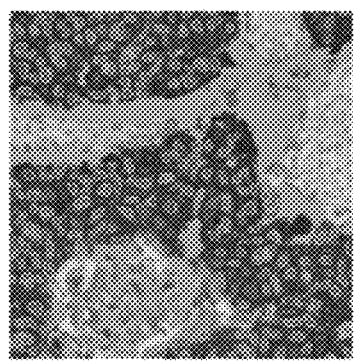
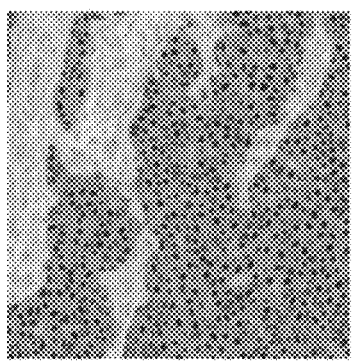
FIGURE 14C  FIGURE 14D

MULTI-SPECTRAL IMAGING INCLUDING AT LEAST ONE COMMON STAIN

CROSS-REFERENCE TO RELATED APPLICATIONS

This application is a continuation of and claims priority under 35 U.S.C. § 120 to U.S. application Ser. No. 12/564,857 filed on Sep. 22, 2009, now U.S. Pat. No. 8,280,134 which claims priority to U.S. Provisional Application No. 61/099,150 filed on Sep. 22, 2008 and entitled "MULTI-SPECTRAL IMAGING INCLUDING AT LEAST ONE COMMON STAIN" the entire contents of which are incorporated herein by reference.

BACKGROUND

Chromogenic staining techniques have been developed empirically to impart visual contrast to various elements within tissue samples. Staining techniques and protocols can produce mixtures of dyes in different tissue elements, and human observers, using microscopes and other imaging devices, have learned to distinguish these staining patterns as typical for particular elements. Modern targeted staining methods, which can be specific to chemical moieties and/or molecular structural arrangements, can produce stained tissues in which two or more chromogenic or fluorescent stains apparently overlap spatially. In fact, the perceived overlap can result because the multiple stains truly are bound within a common structure in the sample, or because, due to the method of preparation, a structure within the sample containing one stain overlaps with a second structure containing a different stain. In either case, it may be difficult to distinguish the presence and relative distribution of the multiple stains and the structures to which they are bound, especially when the stains employed have similar spectral absorption and/or emission characteristics.

In fields such as pathology and cytology in which staining and inspection of tissue samples occurs frequently, the stained samples are often classified according to one or more criteria by human researchers performing visual inspection of the samples using a microscope or other imaging device. For example, a sample can be stained with multiple dyes in order to highlight differences in particular organelles, structures, or molecular targets among cells in the sample. Samples containing different types of cells can be treated with different dyes in order to visually distinguish the number, spatial distribution, and morphology of the cell types. The samples can then be classified according to one or more criteria such as the presence of different types of chemical or biological structures therein. A wide variety of staining protocols have been developed in order to provide different types of classification information for particular classes of samples.

SUMMARY

In general, in a first aspect, the disclosure features a method that includes: providing a sample with M components to be labeled, where M>2; labeling the components with N stains, where N<M so that at least two components are labeled with a common stain; obtaining a set of spectral images of the sample; classifying different parts of the sample into respective classes that distinguish the commonly stained components based on the set of spectral images; and determining relative amounts of multiple ones of the M components in different regions of the sample.

In another aspect, the disclosure features a method that includes: providing a set of spectral images of a sample, where the sample has M>2 components labeled with N<M stains so that at least two components are labeled with a common stain and the sample is further stained with at least one histological stain; classifying different parts of the sample into respective classes that distinguish the commonly stained components based on the set of spectral images; and determining relative amounts of multiple ones of the M components in different regions of the sample.

In a further aspect, the disclosure features a method that includes: labeling multiple components in a sample with one or more stains that emit or absorb with a common spectral distribution; applying a histological stain to the sample; obtaining a set of spectral images of the sample based on at least the stains that label the components and the histological stain; and distinguishing the components labeled with the stains having the common spectral distribution from one another in different parts of the sample based on one or more of signal strength, shape, spectral features, and textural features in one or more of the spectral images that include contributions from at least the histological stain.

In another aspect, the disclosure features apparatus that includes: a means for obtaining a set of spectral images of a sample, where the sample has M>2 components labeled with N<M stains so that at least two components are labeled with a common stain and where the sample is further stained with at least one histological stain; and an electronic processor for analyzing an image stack based on the obtained images and configured to classify different parts of the sample into respective classes that distinguish the commonly stained components based on the set of spectral images.

Embodiments of the methods and apparatus disclosed herein can include any of the following features.

The method can include applying at least one histological stain to the sample prior to obtaining the set of spectral images. The classifying can include distinguishing the commonly stained components from one another in the different parts of the sample based on one or more of signal strength, shape, spectral features, and textural features in one or more of the spectral images that include contributions from the at least one histological stain. The classifying can include: decomposing the set of spectral images into an unmixed image set, where each member of the unmixed image set corresponds to a spectral contribution from a respective one of N stains for labeling the M components or the histological stain; and determining the relative amounts of the multiple ones of the M components based on the unmixed image set.

The classifying can include: decomposing the set of spectral images into an unmixed image set, where each member of the unmixed image set corresponds to a spectral contribution from a respective one of the N stains for labeling the M components and the histological stain; and classifying the different parts of the sample into the respective classes based on an image stack that includes one or more of the unmixed images.

The number of components M can be larger than two (e.g., M>2). The number of stains N can be larger than 1 (e.g., N>1). The N stains can be labeled to the M components as immunohistochemical probes, immunohistological probes, immunofluorescent probes or a combination thereof. The stains can include quantum dots that are labeled to the components by conjugation with antibodies through streptavidin-biotin binding.

The two components that are labeled with a common stain can include nuclear and non-nuclear components of the sample, where the sample is a biological sample. The methods can include applying a counter-stain for nuclei to the sample prior to obtaining the set of spectral images. The classifying can include distinguishing between nuclear components and non-nuclear components in the different parts of the sample based on one or more of signal strength, shape, spectral features, and textural features in the spectral images resulting from at least the counter-stain.

The histological stain can include DAPI, a Hoechst stain, eosin, or hematoxylin.

The determination can be based on the set of spectral images and the classification. The commonly stained components can be distinguished based on one or more of signal strength, shape, spectral features, and textural features in one or more of the spectral images that include contributions from the at least one histological stain.

The classifying can include: decomposing the set of spectral images into an unmixed image set, where each member of the unmixed image set corresponds to a spectral contribution from a respective one of the stains; and classifying different parts of the sample into the respective classes based on an image stack that includes one or more of the unmixed images.

The electronic processor can be configured to determine relative amounts of multiple ones of the M components in different regions of the sample. The classification by the electronic processor can include distinguishing the commonly stained components from one another in the different parts of the sample based on one or more of signal strength, shape, spectral features, and textural features in the image stack resulting from at least the one histological stain.

The electronic processor can be configured to perform the classification by decomposing the set of spectral images into an unmixed image set, where each member of the unmixed image set corresponds to a respective one of the stains, and to classify the different parts of the sample into the respective classes based on an image stack that includes one or more of the unmixed images.

The means for obtaining the set of spectral images can include an RGB camera.

The electronic processor is further configured to perform the determination based on the set of spectral images and the classification.

The electronic processor can be configured to decompose the set of spectral images into an unmixed image set, each member of the unmixed image set corresponding to a spectral contribution from a respective one of the N stains for labeling the M components or the histological stain. The electronic processor can be configured to determine relative amounts of multiple ones of the M components in different regions of the sample based on the unmixed image set.

Embodiments of the methods and apparatus can also include any of the other features disclosed herein, as appropriate.

In another aspect, disclosed is a method that includes classifying different parts of a sample into respective classes based on an image stack that includes one or more images. For example, the sample can be a tissue section.

Embodiments of the method can include any of the following features.

The method can further include decomposing a set of spectral images of a sample into an unmixed image set, where each member of the unmixed image set corresponds to a spectral contribution from a different component in the sample, and where the images in the image stack used for classification include one or more of the unmixed images. For example, the images in the image stack used for classification can include some or all of the unmixed images.

Classifying can include: (i) positioning a sampling window within the image stack to select a portion of the image stack for classification, where the selected portion includes multiple pixels; (ii) classifying the selected portion into one of several classes, where each of the pixels in the selected portion are provisionally classified as having the same class as that of the selected portion; (iii) translating the sampling window to select a second portion of the image stack for classification and classifying the second portion into one of several classes, where each of the pixels in the second portion are provisionally classified as having same class as that of the second portion; (iv) repeating the translating and classifying for the additional portions of the image stack until at least some of the pixels in the image stack have been provisionally classified multiple times as part of different portions selected by the sampling window; and (v) classifying each of at least some of the pixels that have been provisionally classified multiple times into one of the several classes based on their multiple provisional classifications. The different portions selected by the sampling window can include the same number of pixels, and at least some of the different portions selected by the sampling window can overlap with one another. The provisional classifications of each pixel can be expressed as a histogram indicating the number of times the pixel was provisionally classified in each class, and the final classification of each pixel can correspond to the class to which it was most frequently provisionally classified. The number of times at least some of the pixels are provisionally classified can be more than two and no larger than the number of pixels in the sampling window. For example, the number of times at least some of the pixels are provisionally classified can equal the number of pixels in the sampling window. Additionally, the image stack can include only one image.

The image stack can include more than three spectral images, and the classification can include classifying different regions of the image stack into respective classes based on the set of spectral images, where each region includes multiple pixels so that each classification involves both spectral and spatial information.

The method can further include generating a composite image based on a set of spectral images of the sample, where the spatial intensities of two or more different spectral images in the set are weighted differently and combined to produce the composite image, and where the one or more images in the image stack include the composite image. For example, the set of spectral images can include n images, and the one or more images in the image stack used for classification can include fewer than n images. The composite image can be generated by weighting the spatial intensities of the two or more different spectral images in the set according to a function that changes monotonically with a spectral wavelength. The weighting function can be a ramp function that varies linearly with spectral wavelength. Alternatively, the spatial intensities of the two or more different spectral images can be weighted according to a function that changes non-monotonically with a spectral wavelength. For example, the weighting function can include a first portion that changes monotonically with the spectral wavelength and a second portion that changes monotonically with the spectral wavelength, where the slopes of the first and second portions of the weighting function have opposite signs (e.g., the weighting function can be a Gaussian function). The weighting function can be selected to enhance a contrast between features contributed to the composite image from the two or more different spectral images. Further, the one or more images in the image stack can include two or more composite images.

In any of the methods, a neural network can be used for the classifying. Classifying different regions of the sample into the different classes can include identifying selected regions of the image stack that correspond to each of the individual classes, training the neural network to recognize the classes based on the selected regions, and applying the trained neural network to the additional regions of the image stack. The input into the neural network can be a feature vector having one or more elements based on calculating at least one spatial gray level dependency matrix. Alternatively, or in addition, the input into the neural network can be a feature vector having one or more elements based on calculating a two-dimensional Fourier transform.

In certain embodiments, the one or more images in the image stack can include one or more spectral images. The spectral images can be images of sample emission according to different spectral indices for the emission, for example. Alternatively, the spectral images can be images of sample emission according to different spectral indices for illumination of the sample causing the emission. Further, the input information for the classifying can include both spectral and spatial information. The sample can include components having different absorption and emission spectra. In addition, a number of classes into which regions of the sample are classified can be equal to a number of distinct spectral contributors in the sample. For example, the distinct spectral contributors can be chemical dyes or fluorescent labels.

In certain embodiments, the image stack can include an RGB image.

Also, in certain embodiments, one can further include generating an output image showing the classified regions of the sample. Additionally, any of the methods can further include obtaining the one or more images in the image stack. The images can be obtained, for example, by measuring light transmitted through, or reflected from, the sample. The images can also be obtained by measuring fluorescence emission from the sample.

In general, in another aspect, disclosed is a method that includes: (i) positioning a sampling window within an image stack to select a portion of the image stack for classification, where the image stack includes one or more images and the selected portion includes multiple pixels; (ii) classifying the selected portion into one of several classes, where each of the pixels in the selected portion are provisionally classified as having the same class as that of the selected portion; (iii) translating the sampling window to select a second portion of the image stack for classification and classifying the second portion into one of several classes, where each of the pixels in the second portion are provisionally classified as having same class as that of the second portion; (iv) repeating the translating and classifying for the additional portions of the image stack until at least some of the pixels in the image stack have been provisionally classified multiple times as part of different portions selected by the sampling window; and (v) classifying each of at least some of the pixels that have been provisionally classified multiple times into one of the several classes based on their multiple provisional classifications.

Embodiments of the method can include any of the foregoing aspects or features of other methods that are suitable for this method.

In general, in another aspect, the invention features apparatus that includes a computer readable medium storing a program that causes a processor to carry out any of the foregoing methods.

In general, in another aspect, disclosed is an apparatus that includes a means for obtaining one or more images of a sample, and an electronic processor for analyzing an image stack based on the obtained images and configured to classify different parts of the sample into respective classes based on the image stack as set forth in any of the foregoing methods.

Embodiments of the apparatus can include any of the following features.

The means for obtaining the one or more images of the sample can include means for obtaining spectrally-resolved emission images from the sample. The means for obtaining the one or more images of the sample can include means for obtaining images from the sample corresponding to different spectral illuminations of the sample.

In general, in another aspect, disclosed is an apparatus that includes an optical system for obtaining one or more spectral images of a sample, and an electronic processor for analyzing an image stack based on the obtained spectral images and configured to classify different parts of the sample into respective classes based on the image stack as set forth in any of the foregoing methods.

Unless otherwise defined, all technical and scientific terms used herein have the same meaning as commonly understood by one of ordinary skill in the art to which this invention belongs. In case of conflict between documents incorporated herein by reference and the present specification, the present specification will control.

The details of one or more embodiments are set forth in the accompanying drawings and the description below. Other features, objects, and advantages will be apparent from the description and drawings, and from the claims.

DESCRIPTION OF DRAWINGS

FIGS. 14A-D are images of four different antibody probe-labeled samples, each of which has been classified according to unmixed component images for the samples.

Like reference symbols in the various drawings indicate like elements.

DETAILED DESCRIPTION

Overview

Figure 1:
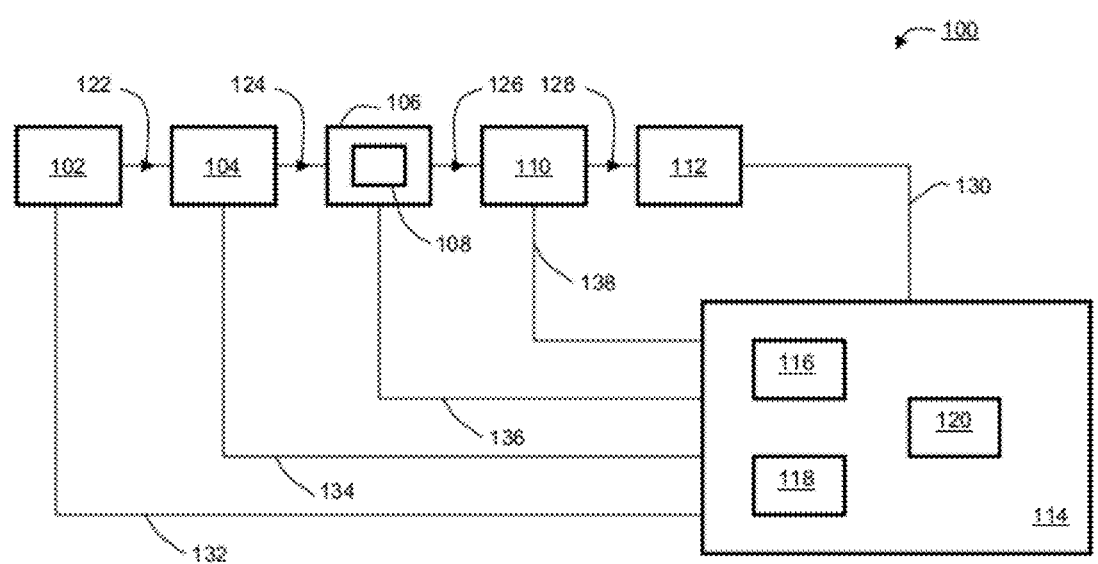
FIG. 1 is a schematic diagram of a system for acquiring spectral images of a sample, and for classifying the sample.

The methods and systems disclosed herein can be used to classify a wide variety of biological and other samples according to spectral and/or structural features appearing on images of the samples. The classification methods include at least some steps that are performed in an automated manner using various machine-vision algorithms and techniques. A set of images of a sample is acquired, and can be transformed prior to submission to an automated classifier. Transformation of the image set can include mathematical transformations such as conversion from intensities to optical densities, spectral unmixing operations, calculation of composite images, and forming a classification data set that may include only a subset of available sample images. The classification data set is then submitted to a machine-based classifier, which can be a neural network or another type of classifier. Image pixels can be classified multiple times, and a final classification performed based on the distribution of the multiple classifications for each pixel. Images illustrating differently-classified regions of the sample can be displayed for a system operator. Classification information can also be used to as an input to direct automated processes such as laser-capture microdissection, or in other image-guided procedures.

The classification methods are mathematical and so are general in scope, and can be applied wherever classification is desired, regardless of the apparatus or method used to obtain the images, or the nature of the sample. The classification methods can be used to classify a wide variety of samples, including samples stained with one or more absorbing stains, and samples that include fluorescent labels. Fluorescent labels can include chemical labels that are introduced into a sample from an external source; alternatively, the labels can be intrinsic to the sample (e.g., endogenous autofluorescence or fluorescent proteins such as green fluorescent protein and red fluorescent protein). The classification methods can also be used to classify samples containing various luminescent species and structures. The images may be obtained in the visible, infrared, or ultraviolet range. The classification methods are not limited to use with images of sample absorption or sample emission, but can also be used to classify images that utilize a wide variety of measurement or contrast mechanisms to visualize a sample, including but not limited to polarized light, sample birefringence, elastic or inelastic light scattering, or fluorescence lifetime.

As used herein, the term "classifying" refers to identifying different regions of an image of a sample that share a set of common characteristics, wherein at least some of the steps in the procedure are performed in an automated fashion by electronic components. The set of common characteristics can include signal strength, shape, spectral and textural features, for example. The identification of such regions in a sample image effectively identifies the corresponding regions in the sample as sharing a set of common features, and more generally that the sample region is of a specific known state or type based on its expression of these features. At least some of the steps in the classification procedure are performed in automated fashion by electronic components. For example, in many embodiments, steps that include spectral unmixing of images, generating composite images, and classifying regions of images into one or more classes are performed by electronic components. However, some operator intervention may occur in other steps. In particular, in some embodiments, steps such as the selection of reference regions corresponding to various classes for training a machine-based classifier may be performed manually by a system operator.

As used herein, "stain" refers to the compound or structure (e.g., a dye or quantum dot) that provides the spectral signature for the stained component of interest. For example, the spectral signature corresponds to the spectral distribution of the emission from a fluorescent stain or the spectral distribution of the absorption from a chromogenic stain.

For the case of immunohistochemical, immunohistological, or immunofluorescent staining, the "stain" is combined with a component that provides molecular specificity so that the combination (i.e., the "probe") can "label" the component of interest. For example, the same quantum dot can be conjugated with different antibodies to thereby label different components with different probes having a common stain (i.e., the quantum dot). Other examples of stains include fluorescent agents such as the Alexa Fluor family of dyes available from InVitrogen (Carlsbad Calif.), and the cyanine family of dyes.

By way of contrast, a histological stain does not provide molecular specificity and does not "label" a compound of interest. Instead, histological stains generally bind to certain physiological structures when applied to a sample. For example, DAPI is a well-known fluorescent dye that can be applied to a biological sample to provide spatial context and landmarks. Specifically, DAPI preferentially binds to nuclei and thereby provides contrast between nuclear and non-nuclear components of the cell, and in some embodiments can serve as a histological stain in the context of the present disclosure. Where the histological stain is spectrally distinct from the stains that label the compounds of interest, the histological stain functions as "counter-stain" to provide physiological spatial context for the labeled compounds. Other examples of histological stains that can be used with the methods and systems disclosed herein include hematoxylin, eosin, Hoechst 33258 and Hoechst 33342.

Methods for labeling compounds in a sample with stains and applying histological stains to the sample are well-known in the art.

In certain embodiments, spectral images of a sample are "unmixed" into images that each correspond to a spectral index of a respective constituent of the sample. These unmixed images can then by processed by the classifier. The use of the unmixed images as the input into the classifier may improve the efficiency and/or accuracy of the classification.

In certain embodiments, one or more composite images can be generated from spectral images, prior to classification. As explained in more detail later, composite images generally include "flattened" spectral information; that is, composite images contain spectral information that is encoded as variations in a spatial intensity image of a sample. The use of the composite image as an input into the classifier may improve the efficiency and/or accuracy of the classification.

In certain embodiments, the classification may involve the use of a sampling window to initially classify the pixels in the window, followed by subsequent translations of the sampling window to make further classifications. The translations are smaller than a dimension of the window, so that pixels are classified multiple times. A final classification of each pixel is then based on the statistical distribution of the initial classifications. The technique enables the use of sampling window large enough to recognize spatial features indicative of a specific class, while still providing fine resolution because of the smaller-scale translations.

In certain embodiments, three or more components in a sample can be labeled with a fewer number of stains so that at least some components are labeled with a common stain. This can simplify the biochemical steps involved in multiple labeling of biological samples because fewer stains are involved. Nonetheless, separate biochemical steps remain for associating the common stain with the different components of interest. The common stain can be used when additional classification techniques can be used to distinguish commonly stained components. For example, a common stain can be used for a nuclear component in a cell and a non-nuclear component in a cell because imaging techniques, such as the machine vision techniques disclosed herein, can be used to distinguish nuclear and non-nuclear regions.

Such embodiments can simplify sample preparation and data acquisition. Specifically, sample preparation can be simplified because such embodiments increase the range and number of targets that can be labeled with commercially available probes. Although there are many commercially available probes for targeting different compounds, it is common that two or more of them share a common stain and are therefore spectrally indistinguishable from one another when used in the same sample. However, the present disclosure enables one to use such commercially available probes to target multiple compounds in the sample in cases where the machine-vision classification techniques disclosed herein can distinguish among the compounds labeled with the common stain. As a result, the embodiments disclosed herein increase the number of targets that can be labeled using commercially available probes. Furthermore, data acquisition of the spectral images can be improved relative to embodiments where every compound of interest is labeled with a different stain. In some embodiments, an improvement is obtained because the light captured by the spectral imaging hardware can be separated into fewer spectral channels, thereby increasing signal-to-noise ratio and detection efficiency. In some embodiments, simple spectral imaging hardware such as an RGB camera can be used to acquire the spectral images as a result of the reduced number of stains involved.

In general, the classification methods disclosed herein can be used to classify features in spectral image sets, including color (RGB) images of a sample and/or more complex spectral image sets including more than three spectral images.

Apparatus for Obtaining Images and Subsequent Classification

FIG. 1 is a schematic diagram showing a system 100 for acquiring multiple spectrally resolved images of a sample, and for classifying the sample. A light source 102 provides light 122 to light conditioning optics 104. Light 122 can be incoherent light, such as light generated from a filament source for example, or light 122 can be coherent light, such as light generated by a laser. Light 122 can be either continuous-wave (CW) or time-gated (i.e., pulsed) light. Further, light 122 can be provided in a selected portion of the electromagnetic spectrum. For example, light 122 can have a central wavelength and/or a distribution of wavelengths that falls within the ultraviolet, visible, infrared, or other regions of the spectrum.

Light conditioning optics 104 can be configured to transform light 122 in a number of ways. For example, light conditioning optics 104 can spectrally filter light 122 to provide output light in a selected wavelength region of the spectrum. Alternatively, or in addition, light conditioning optics can adjust the spatial distribution of light 122 and the temporal properties of light 122. Incident light 124 is generated from light 122 by the action of the elements of light conditioning optics 104.

Incident light 124 is directed to be incident on sample 108 mounted on illumination stage 106. Stage 106 can provide means to secure sample 108, such as mounting clips or other fastening devices. Alternatively, stage 106 can include a movable track or belt on which a plurality of samples 108 are affixed. A driver mechanism can be configured to move the track in order to successively translate the plurality of samples, one at a time, through an illumination region on stage 106, whereon incident light 124 impinges. Stage 106 can further include translation axes and mechanisms for translating sample 108 relative to a fixed position of illumination stage 106. The translation mechanisms can be manually operated (e.g., threaded rods) or can be automatically movable via electrical actuation (e.g., motorized drivers, piezoelectric actuators).

In response to incident light 124, emitted light 126 emerges from sample 108. Emitted light 126 can be generated in a number of ways. For example, in some embodiments, emitted light 126 corresponds to a portion of incident light 124 transmitted through sample 108. In other embodiments, emitted light 126 corresponds to a portion of incident light 124 reflected from sample 108. In yet further embodiments, incident light 124 can be absorbed by sample 108, and emitted light 126 corresponds to fluorescence emission from sample 108 in response to incident light 124. In still further embodiments, sample 108 can be luminescent, and may produce emitted light 126 even in the absence of incident light 124. In some embodiments, emitted light 126 can include light produced via two or more of the foregoing mechanisms.

In many embodiments, sample 108 is a biological sample such as a tissue slice (e.g., a sample used for pathology, or a cell suspension or smear, as in cytology studies), or living or fixed cells in tissue culture. In some embodiments, sample 108 can be an animal (e.g., a mouse), individual bacteria or other microorganisms, bacterial or other colonies, embryos, oocytes, plants, including seeds or grains, or sample 108 can be a non-biological entity.

Light collecting optics 110 are positioned to received emitted light 126 from sample 108. Light collecting optics 110 can be configured to collimate emitted light 126 when light 126 is divergent, for example. Light collecting optics 110 can also be configured to spectrally filter emitted light 126. Filtering operations can be useful, for example, in order to isolate a portion of emitted light 126 arising via one of the mechanisms discussed above from light arising via other processes. Further, light collecting optics 110 can be configured to modify the spatial and/or temporal properties of emitted light 126 for particular purposes in embodiments. Light collecting optics 110 transform emitted light 126 into output light 128 which is incident on detector 112.

Detector 112 includes one or more elements such as CCD sensors configured to detect output light 128. In embodiments, detector 112 can be configured to measure the spatial and/or temporal and/or spectral properties of light 128. Detector 112 generates an electrical signal that corresponds to output light 128, and is communicated via electrical communication line 130 to electronic control system 114.

Electronic control system 114 includes a processor 116, a display device 118, and a user interface 120. In addition to receiving signals corresponding to output light 128 detected by detector 112, control system 114 sends electrical signals to detector 112 to adjust various properties of detector 112. For example, if detector 112 includes a CCD sensor, control system 114 can send electrical signals to detector 112 to control the exposure time, active area, gain settings, and other properties of the CCD sensor.

Electronic control system 114 also communicates with light source 102, light conditioning optics 104, illumination stage 106, and light collecting optics 110 via electrical communication lines 132, 134, 136, and 138, respectively. Control system 114 provides electrical signals to each of these elements of system 100 to adjust various properties of the elements. For example, electrical signals provided to light source 102 can be used to adjust the intensity, wavelength, repetition rate, or other properties of light 122. Signals provided to light conditioning optics 104 and light collecting optics 110 can include signals for configuring properties of devices that adjust the spatial properties of light (e.g., spatial light modulators) and for configuring spectral filtering devices, for example. Signals provided to illumination stage 106 can provide for positioning of sample 108 relative to stage 106 and/or for moving samples into position for illumination on stage 106, for example.

Control system 114 includes a user interface 120 for displaying system properties and parameters, and for displaying captured images of sample 108. User interface 120 is provided in order to facilitate operator interaction with, and control over, system 100. Processor 116 includes a storage device for storing image data captured using detector 112, and also includes computer software that embodies instructions to processor 116 that cause processor 116 to carry out control functions, such as those discussed above for example. Further, the software instructions cause processor 116 to mathematically manipulate the images captured by detector 112 and to carry out the steps of classifying sample 108 according to either or both of the original and the manipulated images. The classification steps are described in more detail subsequently.

In many embodiments, system 100 is configured to acquire multiple spectral images of sample 108. The multiple spectral images may correspond to illumination of sample 108 at a variety of selected wavelengths of light, and detecting an intensity of light either transmitted through or reflected by sample 108. Alternatively, the multiple spectral images may correspond to illumination of sample 108 with light having similar spectral properties, and collecting multiple images of sample 108, each image corresponding to a different wavelength of emitted light 126. Spectral filtering elements in light conditioning optics 104 and light collecting optics 110 are generally used to obtain the spectrally resolved data.

In some embodiments, images of sample 108 can be collected in sequence, with adjustments to the configuration of optical components (e.g., optical filters) between successive captured images. In other embodiments, multiple images can be captured simultaneously using detection systems configured to detect multiple sample views. For example, detection systems can be configured to project different views of the sample corresponding to different illumination or emission wavelengths onto a detector such as a CCD camera, and the multiple views can be captured simultaneously.

In some embodiments, light conditioning optics 104 include an adjustable spectral filter element such as a filter wheel or a liquid crystal spectral filter. The filter element can be configured to provide for illumination of sample 108 using different light wavelength bands. Light source 102 can provide light 122 having a broad distribution of spectral wavelength components. A selected region of this broad wavelength distribution is allowed to pass as incident light 124 by the filter element in light conditioning optics 104, and directed to be incident on sample 108. An image of light 126 transmitted through sample 108 is recorded by detector 112. Subsequently, the wavelength of the filter pass-band in light conditioning optics 104 is changed to provide incident light 124 having a different wavelength, and an image of light 126 transmitted through sample 108 (and corresponding to the new wavelength of incident light 124) is recorded. A similar set of spectrally-resolved images can also be recorded by employing a light source 102 having multiple source elements generating light of different wavelengths, and alternately turning the different source elements on and off to provide incident light 124 having different wavelengths.

As discussed previously, the emitted light 126 from sample 108 can also correspond to incident light 124 that is reflected from sample 108. Further, emitted light 126 can correspond to fluorescence emission from sample 108 if the sample includes fluorescent chemical structures. For some samples, emitted light 126 can include contributions from multiple sources (i.e., transmission and fluorescence) and the spectral filtering elements in light conditioning optics 110 can be used to separate these signal contributions.

In general, both light conditioning optics 104 and light collecting optics 110 include configurable spectral filter elements. Therefore, spectral resolution can be provided either on the excitation side of sample 108 (e.g., via light conditioning optics 104) or on the emission side of sample 108 (e.g., via light collecting optics 110), or both. In any case, the result of collecting multiple, spectrally resolved images of sample 108 is an "image stack" where each image in the stack is a two-dimensional image of the sample corresponding to a particular wavelength. Conceptually, the set of images can be visualized as forming a three-dimensional matrix, where two of the matrix dimensions are the spatial length and width of each of the images, and the third matrix dimension is the spectral wavelength (emission or excitation) to which the image corresponds. For this reason, the set of spectrally resolved images can be referred to as a "spectral cube" of images. As used herein, a "pixel" in such a set of images (or image stack or spectral cube), refers to a common spatial location for each of the images. Accordingly, a pixel in a set of images includes a value associated with each image at the spatial location corresponding to the pixel.

Other arrangements to obtain spectral images which are known in the art may be employed, according to the requirements of the sample at hand.

While each spectral image described above typically refers to a particular wavelength or range of wavelengths (e.g., a spectral band), more generally, each spectral image can correspond to a spectral index that may include one or more wavelength bands, or some more complex spectral distribution. For example, such an image can be generated by using a spectral comb filter. Generally, the image cube will include several spectral images, for example, 10 or more. However, in some embodiments, the image cube may include fewer images, for example, only two or three spectral images. One such example is an red-green-blue (RGB) color image, in which each pixel includes a value associated with the strength of each of the red, green, and blue colors. Such information may be displayed as a single color image, rather than as a set of separate images; however, the information content is the same as that in the set of images, and therefore we use the expression "spectral images" to refer to both cases.

In certain embodiments, images used for classification may also include false-color images, and also monochrome or gray scale images.

Following acquisition of one or more images, sample 108 is classified by system 100 according to the shape, intensity, spectral and/or textural features of the individual image(s). In practice, in some embodiments, images are recorded for multiple samples first, and the classification of the samples is deferred to a later time for expediency.

Not all of the images of a spectral cube need be analyzed in order to accurately classify the sample to which the cube corresponds. In some embodiments, a classification of sufficiently high accuracy is achieved by examining only a subset of the spectral cube images. Further, in some embodiments, the spectrally resolved images may be spectrally unmixed (i.e., decomposed into a set of images corresponding to a set of spectral eigenstates) before analysis. Some embodiments include additional steps wherein one or more composite images are generated via mathematical combination of multiple images selected from the spectral cube and/or the set of spectrally unmixed images. Classification of a sample can be performed based on the composite images, in addition to or exclusive of the spectral cube images and the spectrally unmixed images.

Spectral Unmixing

Figure 2:
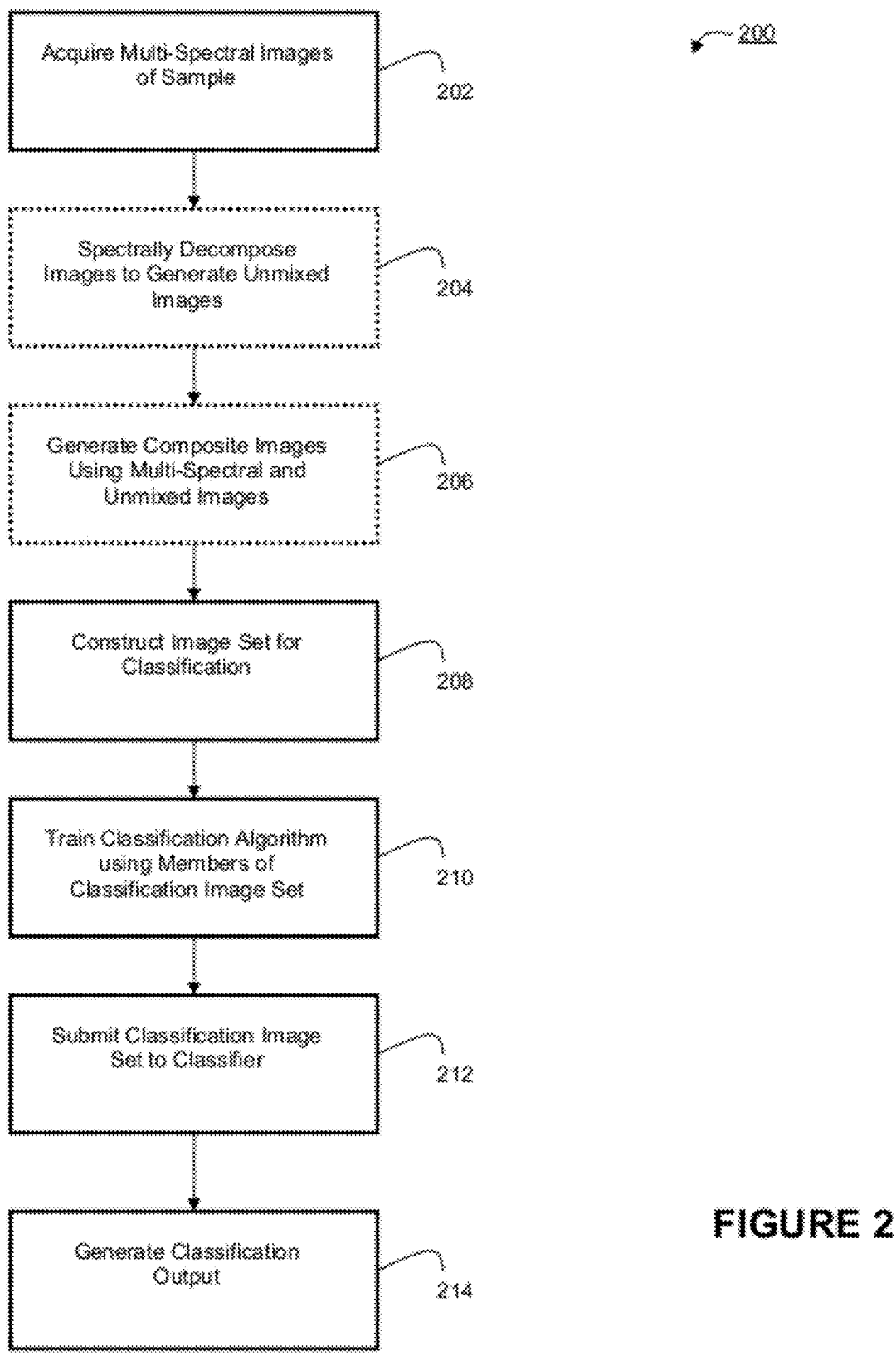
FIG. 2 is a flow chart showing steps involved in classifying a sample.

FIG. 2 is a flow chart 200 showing steps involved in classifying a sample. Step 202 includes acquiring a set of one or more images (e.g., a spectral cube) of a sample, as discussed above. Step 204, which is optional, includes spectrally unmixing some or all of the images in the spectral cube to generate an unmixed set of images (i.e., an "unmixed spectral cube"). Spectral unmixing is a technique that quantitatively separates contributions in an image that arise from spectrally different sources. For example, a sample may contain three different types of structures, each labeled with a different dye. The three different dyes may each have different absorption spectra. Typically, the individual absorption spectra of the dyes are known before they are used, or they can be measured. Images of the specimen under illumination will contain, in the most general case, spectral contributions from each of the three dyes. A similar situation arises, for example, in samples containing multiple different fluorescence labels, each of which contribute to measured fluorescence emissions.

Spectral unmixing decomposes one or more images that include contributions from multiple spectral sources into a set of component images (the "unmixed images") that correspond to contributions from each of the spectral entities within the sample. Thus, if the sample includes three different dyes, each specific to a particular structural entity, then an image of the sample can be separated into three unmixed images, each unmixed image reflecting contributions principally from only one of the dyes.

The unmixing procedure essentially corresponds to decomposing an image into a set of spectral eigenstates. In many embodiments, the eigenstates are known beforehand, as discussed above. In other embodiments, the eigenstates can sometimes be determined using techniques such as principal component analysis. In either case, once the eigenstates have been identified, an image can be decomposed by calculating a set of values, usually as a coefficient matrix, that corresponds to the relative weighting of each of the eigenstates in the overall image. The contributions of each of the individual eigenstates can then be separated out to yield the unmixed image set.

As an example, a series of two dimensional images having x and y coordinates can be measured for a sample by illuminating the sample at a set of different excitation wavelengths $\lambda_k$. As described above, the two dimensional images can be combined to form a three-dimensional image cube I(x,y,k) where the first two indices of the image cube represent coordinate directions, and the third index is a spectral index corresponding to the wavelength of the illumination light. Assuming, for the sake of simplicity, that each of the images of the sample contains spectral contributions from two different spectral sources $F(\lambda_k)$ and $G(\lambda_k)$, then the values in the three-dimensional image cube I(x,y,k) may be given by $$S(x,y,k) = a(x,y) \cdot F(\lambda_k) + b(x,y) \cdot G(\lambda_k) \qquad (1)$$

where $\lambda_k$ is used to denote a given wavelength (or wavelength band). The functions a(x,y) and b(x,y) describe the spatial abundance of the spectral contributions from the two different spectral sources in the sample.

According to Equation (1), the net signal any position in the three-dimensional image cube (i.e., at any two-dimensional pixel coordinate, and at a particular illumination wavelength) is the sum of two contributions, weighted by the relative abundance of each. This can be expressed as $$I(\lambda_k) = aF(\lambda_k) + bG(\lambda_k) \qquad (2)$$

The functions F and G can be termed the "spectral eigenstates" for the system because they correspond to the pure spectra for the spectral sources in the sample, which are combined in varying proportions to produce the measured spectral images of the sample. Thus, the sample spectrum is a weighted superposition corresponding to separate contributions from the two spectral sources.

If the spectra $F(\lambda_k)$ and $G(\lambda_k)$ are known (or can be deduced), then Equation (2) can be inverted to solve for a and b, provided that spectrum I includes at least two elements (i.e., provided that one has data for at least two wavelengths $\lambda_k$). Equation (2) can be rewritten in matrix form as I=EA, so that $$A = E^{-1} I \qquad (3)$$

where A is a column vector with components a and b, and E is a matrix whose columns are the spectral eigenstates, namely [F G].

Using Equation (3), measured spectral images of a sample can be used to calculate contributions to the images arising purely from source F and purely from source G at particular pixel locations. The process can be repeated for each pixel location on a selected image (i.e., throughout the range of values x and y in I) to produce an image of the sample that includes contributions only from source F, and another image of the sample that includes contributions only from source G.

In the above discussion, the number of spectral sources is two (i.e., F and G). In general, however, unmixing techniques are not restricted to any particular number of sources. For example, a sample can generally contain m different spectral sources. If the number of wavelengths at which data is collected is n—that is, k=1 ... n—then matrix E is an n×m matrix instead of an n×2 matrix, as in the above discussion. The unmixing algorithm can then be employed in the same manner as described above to isolate specific contributions at each pixel location in an image from each of the m spectral eigenstates.

One factor which can limit the ability of the algorithm to distinguish between contributions from different spectral eigenstates is the degree of spectral distinction between the eigenstates. The correlation between two spectra, such as two spectral eigenstates $I_1$ and $I_2$, can be described by a spectral angle θ where $$\theta = \cos^{-1}\left[\frac{I_1 \cdot I_2}{|I_1||I_2|}\right] \quad (4)$$

Sets of spectra for which θ is small for two members are not as easily separated into their components. Physically, the reason for this is easily understood: if two spectra are only marginally different, it is harder to determine the relative abundance of each.

A number of techniques can be used to measure or estimate the pure spectra of the spectral sources F and G (and other spectral sources, where the sample includes more than two). In general, any method that yields spectral eigenstates of sufficient accuracy can be used. Some samples can contain spectral sources such as dyes, fluorescence labels, or other chemical moieties for which there are known spectra available in published reference materials. Alternatively, it may be possible to directly measure the spectra of source components using one or more measurement systems. In some samples, a particular region of the sample may be known to include only one particular spectral source, and the spectrum of that source can be extracted from measurements taken on only the identified region of the sample.

Various data analysis techniques can also be used for determining component spectra for spectral unmixing, such as principal component analysis (PCA), which identifies the most orthogonal spectral eigenvectors from an image cube and yields score images showing the weighting of each eigenvector throughout the image. This may be done in combination with other mathematical processing, and there are other known techniques for identifying low-dimensionality spectral vectors, such as projection pursuit, a technique described, for example, in L. Jimenez and D. Landgrebe, "Hyperspectral Data Analysis and Feature Reduction Via Projection Pursuit", *IEEE Transactions on Geoscience and Remote Sensing*, Vol. 37, No. 6, pp. 2653-2667, November 1999, the entire contents of which are incorporated herein by reference. Other techniques include independent component analysis (ICA) and end-member detection algorithms, for example.

These techniques are typically not well-suited to the applications in the life sciences. For example, some techniques are optimized for spectral imaging data sets that contain spectra with dense spectral shapes and well-defined narrow peaks. In some techniques the spectral ranges are large compared to the individual spectral features and peaks that are used for analysis. The presence of peaks, or the ratio of peaks may be then used to classify "end-members" to be separated. Unfortunately, the components in biological samples typically do not have such well-defined, narrow peaks.

Some of these techniques generate images related to spectra that are present in a pure form somewhere within the original image cube. In many cases in the life sciences, signal spectra present in the image cube are mixtures of components. If the component of interest is not in a pure form somewhere in the original image cube, then it is unlikely that these techniques will generate an image that accurately represents the abundance of the component of interest.

There are some techniques, sometimes called "convex-hull" algorithms, that estimate what the true end-members are even if they do not exist in a pure form in the image, but the effectiveness is dependent on how close signal spectra in the image cube are to the end-members.

One technique that can be used to extract spectral eigenstates (or representations thereof) without a priori knowledge of all of the eigenstates involves considering the signal spectrum $I(\lambda_k)$ for a given pixel, and subtracting from it the maximum amount of a first spectral source $F(\lambda_k)$ while leaving the remaining signal that is positive definite in all spectral channels. That is, one defines a so-called "remainder spectrum" $U_a(\lambda_k)$ for each pixel as $$U_a(\lambda_k) = I(\lambda_k) - aF(\lambda_k) \quad (5)$$

and then selects the largest value of the parameter a consistent with $U_a(\lambda_k)$ having a non-negative value in every spectral channel. The resulting spectrum $U_a(\lambda_k)$ is then used as the signal spectrum, expunged of contributions due to first spectral source F. One may also make the determination of parameter a based not on strict non-negative criterion listed above, but on some related criteria that incorporates a small negative distribution, to account for considerations such as shot noise or detector noise in a measurement system. Additional examples of optimization criteria for removing the maximal amount of spectral source F include using different error functions.

Alternatively, one may seek to extract a contribution to a measured spectrum that is due to second spectral source G. In analogy with Equation (5), the remainder spectrum can be calculated for each pixel as $$U_b(\lambda_k) = I(\lambda_k) - bG(\lambda_k) \quad (6)$$

where one selects the largest value of the parameter b consistent with $U_b(\lambda_k)$ having a non-negative value in every spectral channel.

The remainder technique can be expanded to cases where the spectra for one or more additional components of the sample are known, and one wants to remove their contributions to the signal. In such cases, the remainder spectrum is written to subtract a contribution of each such component from the observed signal based on the additional spectra and consistent with a positive remainder in each spectral channel.

Additional spectral unmixing techniques are described in PCT Patent Publication No. WO2005/040769 entitled "SPECTRAL IMAGING OF BIOLOGICAL SAMPLES" by Richard Levenson et al., the contents of which are incorporated herein by reference.

In order for the spectral unmixing techniques disclosed herein to effectively separate contributions in sample images that are due to different spectral eigenstates, Equation (1) should be at least approximately correct. That is, the measured spectral data should be approximately described as a linear superposition of weighted eigenstates. This approximation holds for many samples and spectral measurement techniques, especially darkfield measurement techniques. For example, sample images arising from fluorescent or luminescent chemical labels within the sample typically satisfy the linearity assumption. In some cases however, such as for some brightfield measurement techniques, the linearity approximation may not be satisfied. For example, when images are captured that arise from illumination light that is transmitted through a sample that includes light-absorbing components, the linearity assumption in Equation (1) may not be correct. Instead, the intensity of the measured light may be reduced with an exponential dependence on the concentration of the light-absorbing components. In such cases, transformation of the images may first be necessary before unmixing techniques can be used. As an example, for sample images measured in a transmission mode, the measured image intensities can be transformed into optical densities (e.g., by applying a logarithmic function) in order to apply linear unmixing techniques. Optical density techniques are further described, for example, in U.S. application Ser. No. 10/226,592 (Publication No. US 2003/0081204 A1) entitled "SPECTRAL IMAGING" by Paul J. Cronin and Peter J. Miller, filed Aug. 23, 2002, the entire contents of which are incorporated herein by reference.

Spectral unmixing operations (e.g., matrix inversion techniques and remainder techniques) and image data transformation operations (e.g., converting measured image intensities to optical densities, where appropriate) can be performed by electronic control system 114 via processor 116, for example. These operations can include manual intervention and configuration steps performed by a system operator, or system 100 can be configured to perform these operations in an automated manner.

Composite Images

Application of the unmixing techniques discussed above provides a set of unmixed images from a multi-spectral data set. Returning now to FIG. 2, in a second optional step in flow chart 200, step 206 includes generating one or more composite images using the spectral cube images and/or unmixed spectral cube images. Composite images are generated as a means to "flatten" or compress spectral information into a two-dimensional grayscale image. In other words, in terms of a 3D spectral matrix of image data, generating a composite image corresponds roughly to compressing or packing the information from two or more layers into a single layer. Since both spectral cube and unmixed spectral cube image data can be used, the technique can conceptually include packing multiple layers from different spectral cubes into a single layer.

As an example, consider a 3D spectral cube of images, where each image has width x, height y, and an index k that corresponds to a wavelength $\lambda_k$. If there are a total of N different images in the cube (i.e., data recorded at N different wavelengths) then the spectral cube I can be represented, as described previously, as a matrix I(x,y,k). Compressing spectral information from two or more images in the spectral cube to create a composite image C is equivalent to adding the image layers together. In some embodiments, prior to adding the layers together, each layer is scaled according to a weighting function $f(k)$. The spectral compression operation is then performed according to $$C(x, y) = \sum_{k=m}^{n} f(k) \cdot I(x, y, k) \quad (7)$$

which yields composite image C(x,y) from layers m through n of the spectral image cube. The weighting function $f(k)$ is generally chosen to emphasize different spectral features in the composite image; that is, to create contrast between features arising from the different layers of the spectral cube that contribute to the overall intensity distribution in the composite image.

A wide variety of weighting functions can be chosen in order to produce the desired contrast. In general, in some embodiments, a monotonically increasing or decreasing function is chosen for $f(k)$, such as a linear ramp function or a sigmoidal function. In other embodiments, $f(i)$ can be a dual ramp function (i.e., decreasing to a point and then increasing, or increasing to a point and then decreasing) or another function, such as one or more Gaussian functions. The weight function can generally be selected as desired, and can be applied to a batch series of samples, or can be selected individually for each sample prior to classification. System 100 can include a storage medium to store weighting functions for particular types of samples, so that a weighting function appropriate for a sample undergoing classification can be recalled as needed.

Step 208 includes selecting a set of images to be classified. In general, any or all of the images from the spectral image cube, the unmixed spectral image cube (if calculated), and the composite images (if calculated) can be selected for classification analysis. In some embodiments, for example, classification of a sample to a high degree of accuracy can be achieved using a composite image and a small subset of either spectral cube images or unmixed spectral cube images. This has the advantage that the overall set of data upon which a classification algorithm operates is greatly reduced, increasing the speed with which the classification of the sample is complete.

In some other embodiments, images from the unmixed spectral cube can be used for sample classification. The images can be delivered to a classification algorithm, and may be accompanied (although not always) by one or more composite images.

In some embodiments, more than three spectral images can be used for classification of a sample. The images can be taken from either the spectral image cube or, if calculated, an unmixed spectral image cube. This technique can be particularly advantageous when the sample includes more than three distinct spectral contributors. For example, the sample can contain four different stains or dyes, or four different fluorescent labels.

In other embodiments, color RGB images or single plane images can be used for classification of a sample. Single plane images may be narrow band or panchromatic.

Classification

In general, the classifier is a mechanism or rule-set to assign a sample to one of several output classes, and it can be any linear or nonlinear classifier. Linear classifiers include least-squares distance, Mahalanobis distance, and others. These may be used, but the classifier is preferably a machine-learning algorithm such as a neural network, genetic algorithm, or support vector machine. However, a neural network is often preferred, and will be used as the example throughout the subsequent discussion.

The neural network is generally applied to one or more areas, each of which typically corresponds to several pixels (e.g., a 2×2 set of pixels, or a 16×16 set of pixels, etc.) in the image stack (which, as described above, may include one or more images). When there is more than one image in the image stack, each pixel will include a value associated for each of the images. The values for all of the pixels in a given area being classified form the basis of the input information that can potentially be applied to the neural network. Because each area includes several pixels, the input information available to the neural network includes both spatial and spectral information when the image stack includes a composite image and/or multiple spectral images.

The neural network has one or more input nodes, by which it receives information about the region to be classified. An input is termed a "feature vector," where each element of the feature vector corresponds to a specific input node of the neural network. The elements of the feature vector are functions of the signal values at one or more pixels in the area being classified. Examples of suitable functions for producing the feature vector are described further below.

The neural network will also have several output nodes, each corresponding to a class to which the area may be designated. When the feature vector for a given area is applied to the neural network, values for the output nodes correspond to the degree to which the area should be assigned to a given class. Preferably, the neural network is trained so that the output node values are binary, with only one output node yielding a non-zero value (and indicating the class to which the area should be assigned) for any given feature vector.

As described in further detail below, the neural network is trained and can be further optimized to reduce the number of input nodes necessary for efficient and accurate classification. In many embodiments, the use of unmixed images and/or one or more composite images can lead to a reduction in the number of input nodes, and therefore greater efficiency when classifying the regions of an unknown sample. The topology of the neural network employed in some embodiments is bipolar, although binary and other neural network types can also be used effectively. The network is trained using a back propagation method, with momentum included in the training algorithm. The activation function of the network in some embodiments is a bipolar sigmoidal function; other activation functions can also be used.

In embodiments, the networks can commonly include 0, 1, or 2 hidden layers, which are the layers between a first layer having the input nodes and the last layer having the output nodes, although additional hidden layers are possible. Anywhere from 1-15 nodes per hidden layer and are common, though again additional nodes can be used. The input layer of the network uses spatial and spectral texture features identified on sample images as input. The output layer includes a number of output nodes equal to the number of identified classes $N_c$.

Figure 11:
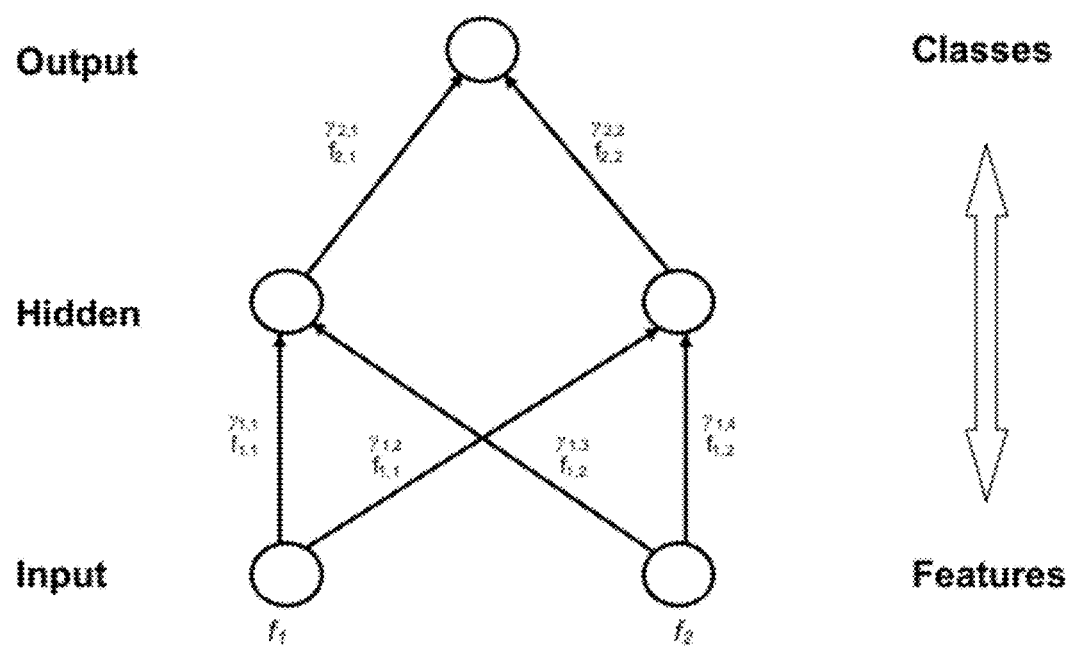
FIG. 11 is a schematic diagram of a portion of a neural network.

FIG. 11 is a schematic diagram showing an example of a neural network that can be used in the classification methods disclosed herein. The network includes an input layer, one hidden layer, and an output layer. Inputs to the neural network are feature vectors $f_m$, and coupling strengths between nodes are given by $\gamma_{k,l}$ values. The outputs from the neural network are the classes associated with an image or image stack.

Typical topological parameters for networks used in the processing of tissue sample images include one hidden layer with 5 nodes, a learning parameter of 0.2, and a momentum factor of 0.5. The structure of neural networks are described, for example, in Christopher M. Bishop, "Neural Networks for Pattern Recognition", Oxford University Press, 1995.

Referring again to FIG. 2, after selecting the set of images according to which the sample will be classified (the "classification image set"), step 210 includes training the classifier using images from the classification image set.

The neural network is trained when a new type of sample is presented for classification analysis. A system operator can be provided with a choice to re-train the existing network for a particular sample via display device 118, for example. The procedure for training the neural network is discussed in greater detail subsequently.

After the neural network-based classifier is trained, step 212 includes submitting the classification image set to the classifier. The classifier generally classifies portions of the sample according to textural and spectral features present on images of the sample in the classification image set. The details of the steps involved in the classification routine are presented later.

Finally, step 214 includes generating classification output for the sample. The classification output can include, for example, one or more images constructed to show contrast between differently classified regions of the sample. Alternatively, or in addition, the classification output can include warning sounds or messages to indicate the presence or absence of particular elements (i.e., stained or labeled structures) in the sample. The output can also include numeric data indicating the types of regions present in the sample, their relative abundance, and other numerical parameters describing the sample.

Training the Neural Network

Figure 3:
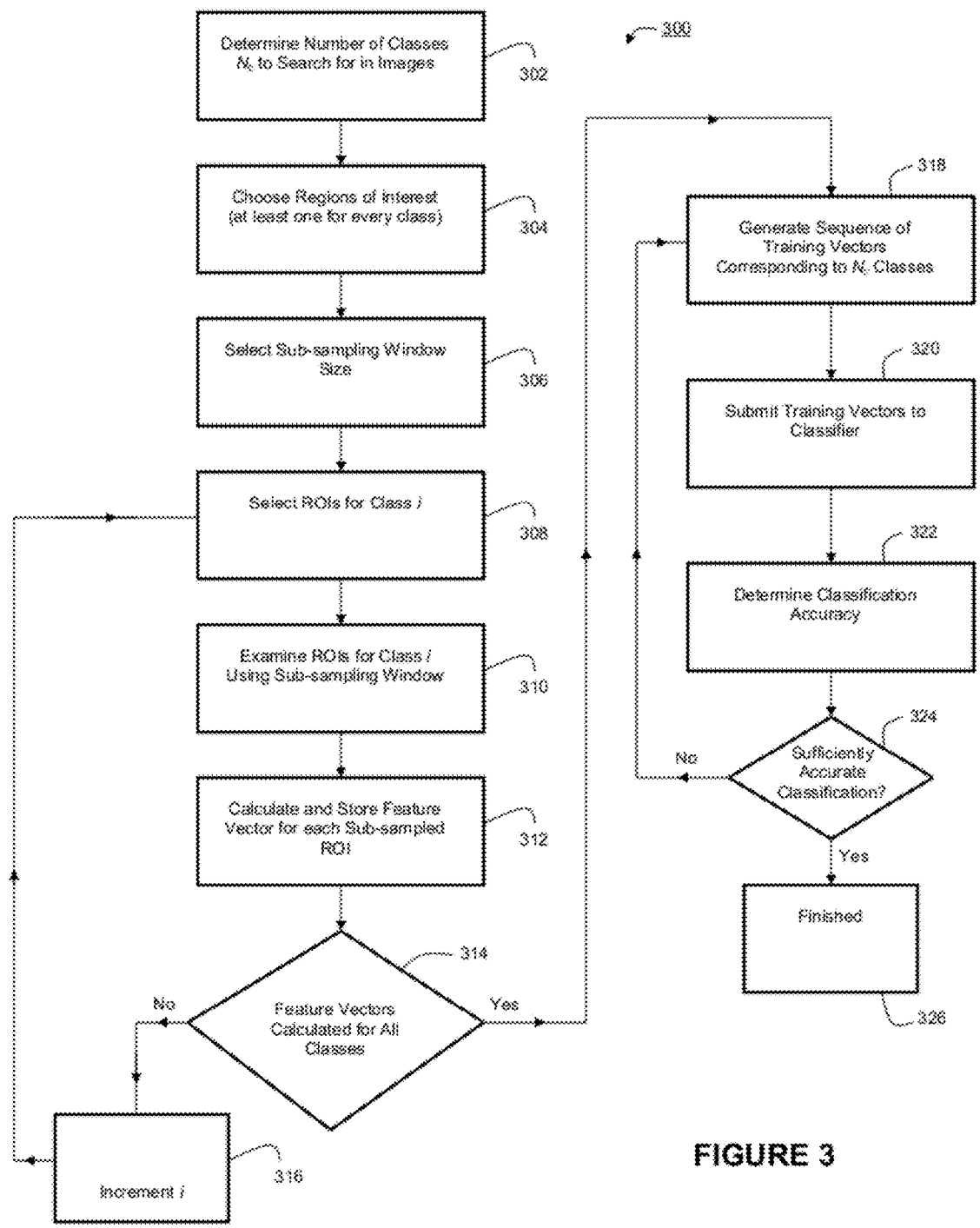
FIG. 3 is a flow chart showing steps involved in training a neural network to perform sample classification.

FIG. 3 is a flow chart 300 that includes steps for training the neural network classifier. A first step 302 includes determining a number of classes Ar, to search for in the image stack. In many embodiments, the number of classes is selected to correspond to the number of different states that are expected or sought within the sample. This may be greater than the number of spectral planes in the image set, or it may be fewer. For example, a sample may be stained with three different dyes or labeled with three different fluorescent labels. In such a sample, one may seek to identify three different classes $N_c$, or two, or five, according to the structure and nature of the sample. The classifier is capable of resolving more classes $N_c$ than the number of spectral planes, based on other aspects of the sample such as signal strength, shape, and texture.

The second step 304 includes selecting at least one training region of interest (ROI) for every class on one of the sample images (the pixel spatial coordinates (x,y) of the ROIs for each of the classes are assumed to be the same from one image to the next). The training ROIs are known to correspond to respective classes and provide a reference for the neural network algorithm to allow it to determine particular spectral and spatial features which are common to each of the classes in order to assist in classification decisions. In some embodiments, for example, the selection of ROIs occurs dynamically via interaction with a system operator through display device 118 and user interface 120.

The third step 306 includes selecting a sub-sampling window size. A sub-sampling window is used to examine each of the selected ROIs at a finer level of detail. In many embodiments, the sub-sampling window size is chosen to be smaller than the mean length and width of all of the ROIs, but larger than a single pixel within the ROI. The sub-sampling window width is also frequently chosen to have both width and length that are multiples of 2, because Fourier methods that operate on sub-sampled regions of the ROIs can take advantage of FFT algorithms if the variable space is a multiple of 2. In embodiments, typical sub-sampling window sizes include 4×4 pixels, 8×8 pixels, 16×16 pixels, and 32×32 pixels, although a wide variety of window sizes, including window sizes not listed explicitly herein, are also possible. Moreover, while the presently described embodiments presume that the data for each image is represented with respect to a two-dimensional grid of squares, other embodiments may include a different representation of data and corresponding window and ROI dimensions. For example, the data may represented on a hexagonal grid, or some other shape.

Figure 4:
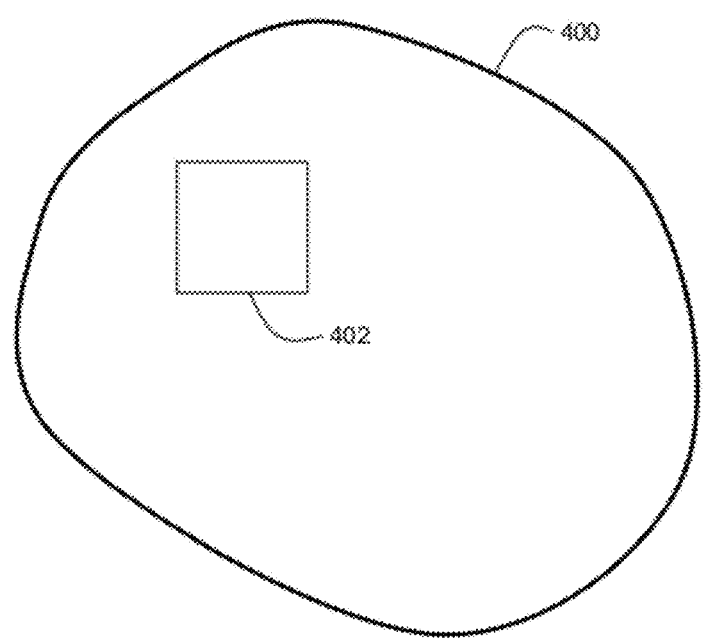
FIG. 4 is a schematic diagram showing a region of interest selected for a particular class.

The next series of steps involve operations conducted on each of the identified classes. Each of the classes is analyzed in turn. Step 308 includes selecting a ROI corresponding to a currently selected class. Step 310 includes examination of the ROI by sub-sampling the ROI with the selected sub-sampling window. FIG. 4 shows the sub-sampling process in greater detail. A chosen ROI 400 is sub-sampled by a sub-sampling window 402 that selects a fraction of the image pixels within ROI 400 for analysis.

Returning to FIG. 3, step 312 includes calculating and storing a feature vector for each of the sub-sampled regions of the ROI. The feature vector includes as elements a set of numbers calculated from the sub-sampled pixels of the ROI. Each of the calculated feature vectors correspond to a feature vector that would, for a properly trained neural network, output a classification corresponding to the selected class. The elements of the feature vector generally correspond to particular texture analysis features which provide a basis for classification of regions within an image of the sample.

Many different numerical quantities can be calculated in order to provide a sufficiently distinguishable description of the ROI. For example, in some embodiments, the feature vector corresponding to a selected ROI for a particular class can include 10 different calculations for each of the images in the image stack, thereby resulting in vector with $10 N_i$ elements, where $N_i$ is the number of images in the image stack. The first four of the ten calculations can be texture analysis features obtained from spatial gray level dependency matrices (SGLDMs), which are also referred to as co-occurrence matrices. For example, such matrices are described in R. M. Haralick, K. Shanmugam, and I. Dinstein, "Textural features for image classification", *IEEE Trans. Syst., Man, Cybern.*, vol. SMC-3, pp. 610-621, 1973. A SGLDM is a spatial histogram of an image (or a portion thereof) that quantifies a distribution of gray scale values within the image. SGLDMs can be calculated, for example, from an estimate of the second-order joint conditional probability densities, $s_\theta(i,j|d,\theta)$. Each value of this conditional probability density represents the probability of a pixel having a gray level value i being d pixels away from a pixel having a gray level value j in a direction described by $\theta$. If an image includes $N_g$ gray levels, then an $N_g \times N_g$ matrix $s_\theta(i,j|d,\theta)$ can be created. Optionally, the matrix can be summed over a set of directions $\theta$ for a selected distance d. For example, in some embodiments, a single direction $\theta=0°$ can be selected. In other embodiments, for example, four directions can be employed: $\theta=0°, 45°, 90°$, and $135°$. In general, any number of directions can be selected for analysis of the texture features in a particular ROI.

In some embodiments, the distance d is fixed at a particular value for analysis. For example, the distance d can be fixed at a value of 1 pixel. In other embodiments, a range of distances can be used, depending upon the nature of the specific texture features. In general, the distance d and the direction $\theta$ can be regarded as parameters that are adjusted in order to ensure higher accuracy classification performance from the neural network.

With four directions $\theta$ and a single fixed distance d of one pixel, for example, a SGLDM can be computed as a sum of co-occurrence matrices over the four directions in each ROI. Textural features can then be calculated from each SGLDM. For example, four different textural features that can be calculated from each SGLDM include energy (E), entropy (S), local homogeneity (H), and inertia (R). The inertia value is also referred to as "contrast". In this example, then, four SGLDM features for the set of angles $\theta$ can be calculated as follows for each ROI:

$$E = \sum_{i=0}^{N_g-1} \sum_{j=0}^{N_g-1} [s_\theta(i, j | d)]^2 \qquad (8)$$

$$S = \sum_{i=0}^{N_g-1} \sum_{j=0}^{N_g-1} s_\theta(i, j | d) \log[s_\theta(i, j | d)] \qquad (9)$$

$$H = \sum_{i=0}^{N_g-1} \sum_{j=0}^{N_g-1} \frac{1}{1+(i-j)^2} s_\theta(i, j | d) \qquad (10)$$

$$R = \sum_{i=0}^{N_g-1} \sum_{j=0}^{N_g-1} (i-j)^2 s_\theta(i, j | d) \qquad (11)$$

where $s_\theta(i,j|d)$ corresponds to the (i,j)-th element of the SGLDM for a distance d. The calculated values E, S, H, and R, for each of the image slices, can then be stored as the first 4N elements in the feature vector corresponding to the ROI for the currently selected class.

Figure 9:
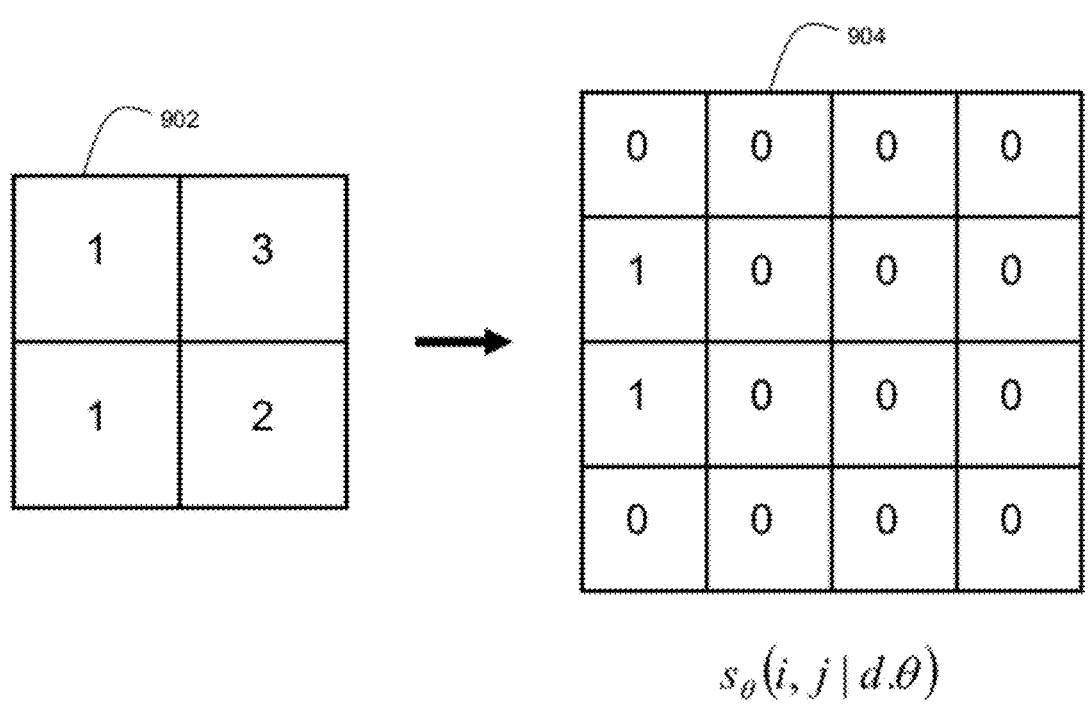
FIG. 9 shows a calculation of a spatial gray level dependency matrix.

As an example, a 2×2 region 902 of an image is shown in FIG. 9. The region includes 4 pixels, each of which can have an integral intensity level from 1 to 4 (i.e., $N_g=4$). The second-order joint conditional probability matrix $s_\theta(i,j|d\,\theta)$ is therefore a 4×4 matrix 904. In order to evaluate the numerical elements of matrix 904, particular values of d and $\theta$ can be selected. For example, selecting $\theta=0$ corresponds to evaluating probabilities along rows of region 902. Selecting d=1 corresponds to evaluating probabilities for elements in region 902 that are separated by 1 unit (i.e., adjacent elements). With the selection of $\theta=0$ and d=1 for region 902, the values of the elements of probability matrix 904 are as shown in FIG. 9.

Figure 5:
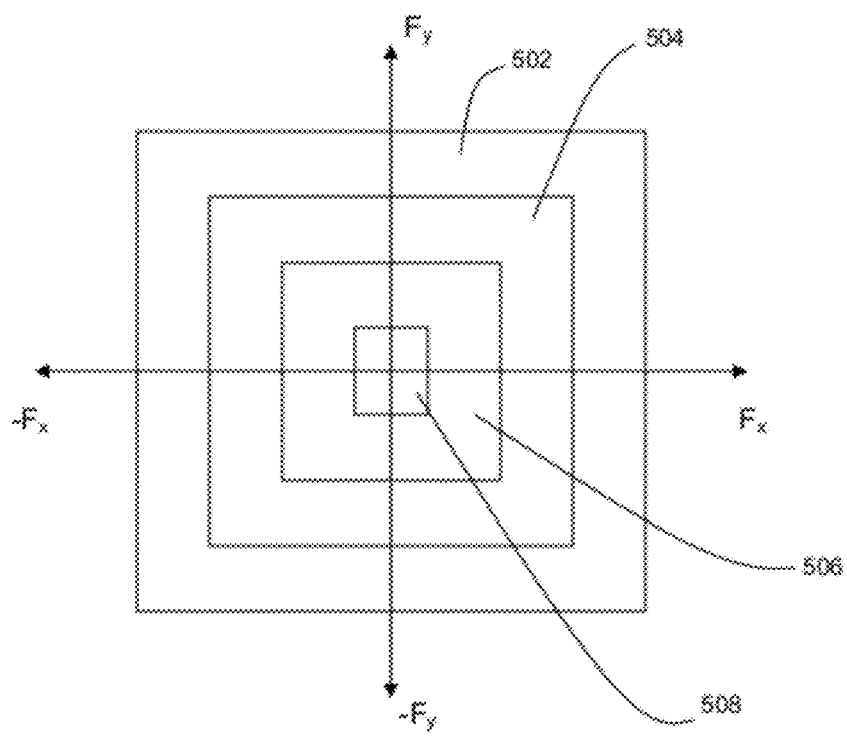
FIG. 5 is a schematic diagram showing a partitioning of a spatial Fourier transform of a sample image in frequency space into a set of smaller regions.

In region 902, pixel (1,1) has an intensity value of 1. Related to pixel (1,1), at a distance d=1 and angle $\theta=0$, is pixel (1,2) with an intensity value of 3. Therefore, the probability value at position (3,1) in matrix 904 is 1. Pixel (2,1) in region 902 has an intensity value of 1. Related to pixel (2,1) at a distance d=1 and angle $\theta=0$ is pixel (2,2) with an intensity value of 2. Therefore, the probability value at position (2,1) in matrix 904 is 1. In some embodiments, the next four calculations for each of the image slices in the ROI's feature vector can be derived from the magnitude of the complex 2D Fourier transform of the ROI. For example, the 2D Fourier transform can be calculated (e.g., using a 2D FFT algorithm, if the sub-sampling window width and length are multiples of 2) and the magnitude data stored in a matrix, wherein the DC frequency component is represented by the origin of the axis in the frequency domain. FIG. 5 is a schematic illustration of a sub-sampled ROI for which a 2D Fourier transform is calculated. The 2D Fourier transform data set can then be divided into four concentric regions 502, 504, 506, and 508 based on frequency content. The outermost region 502, for example, represents a portion of the sample image having the highest spatial frequency content.

The magnitudes of the spatial frequencies in each of regions 502, 504, 506, and 508 can be integrated and normalized to the total signal magnitude. The integrated magnitudes form the next four elements in the ROI's feature vector, and each corresponds to a percentage of Fourier transform signal within a certain range of spatial frequencies.

In general, in embodiments, the spatial Fourier transform data can be partitioned into any number of selected frequency regions (subject to the spatial Nyquist limit) and the integrated intensities from these regions correspond to textural features of the image. Some or all of these textural features can be incorporated into the feature vector for the ROI.

The remaining two calculations in this present example of determining the feature vector can be derived from first order pixel statistics. For example, the ninth and tenth calculations can correspond to the mean and standard deviation of the pixel values within the ROI. In general, other statistical measures can also be useful as feature vector elements. These quantities can be derived from first order or higher order statistical measures (e.g., the variance in pixel values, which is derived from the second moment of the statistical distribution of pixel values).

Referring again to FIG. 3, following calculation of each of the elements of the feature vector that corresponds to the currently selected class, the feature vector is stored. A logical decision 314 follows next. If feature vectors for all of the $N_c$ classes have been calculated and stored, then subsequent neural network training steps, beginning with step 318, are taken. Conversely, if feature vectors have not been calculated, then in step 316 a class indicator is incremented, which is equivalent to selecting a new class and its associated ROI, and the analysis for the newly selected class begins at step 308.

When all of the feature vectors for the identified classes have been calculated, the next step in the sequence is step 318, which includes selecting a sequence of the calculated feature vectors for use as training vectors corresponding to the $N_c$ classes identified in step 302. The set of training vectors can include multiple vectors corresponding to different ROIs for each of the classes. However, care is taken to ensure that each identified class contributes the same number of distinct training vectors to the training set in step 318. This balancing of the relative abundance of different training vectors in the training set is important in order to ensure that the neural network is trained in unbiased fashion with respect to the different classes in sample images.

In step 320, the set of training vectors is submitted to the neural network-based classifier for classification. The vectors are classified one-by-one in random order, and for each one the neural network develops an output estimate of what class the vector belongs to, and this is compared against the actual known class corresponding to the vector. The difference between the network output and the actual class is termed the error. The network is then adjusted using a method such as gradient descent back-propagation, or other error-adjustment techniques, which acts to adjust the network values and produce a reduced error value. When all of the training ROIs have been assigned by the network, the classification accuracy can be determined in step 322, either manually by an operator or automatically by calculating a score that indicates, for example, what percentage of ROIs were classified correctly.

Logical step 324 includes a decision based on the accuracy of the classification of the training ROIs. If the accuracy is higher than a selected threshold (which, in some embodiments, can be set to 100% accuracy, for example) then the neural network is considered to have been suitably trained and the training sequence finishes in step 326. However, if the accuracy falls below the selected threshold, then the steps involving classification of training ROIs are repeated. That is, training vectors are prepared as in step 318 and test classification of these ROIs by the neural network begins again. The vectors may be the same set used in the initial training, or may be a different set of vectors. Repeatedly training on a single set is productive as long as the error network adjustment continues to improve classification accuracy. In many embodiments, 100% accuracy is achieved on a first set of training ROIs. However, the threshold for successful training may be set lower than 100 percent if that is desirable. This may occur if one does not have perfect knowledge of class identity for the training ROIs, or if the samples themselves are highly variable and a wide range of training ROIs are employed.

Optimizing the Neural Network

Following successful training of the neural network-based classifier, the network can optionally be optimized with respect to the number of features used to classify sample images. Optimizing the network in this manner can increase the efficiency and speed of classification operations.

Figure 6:
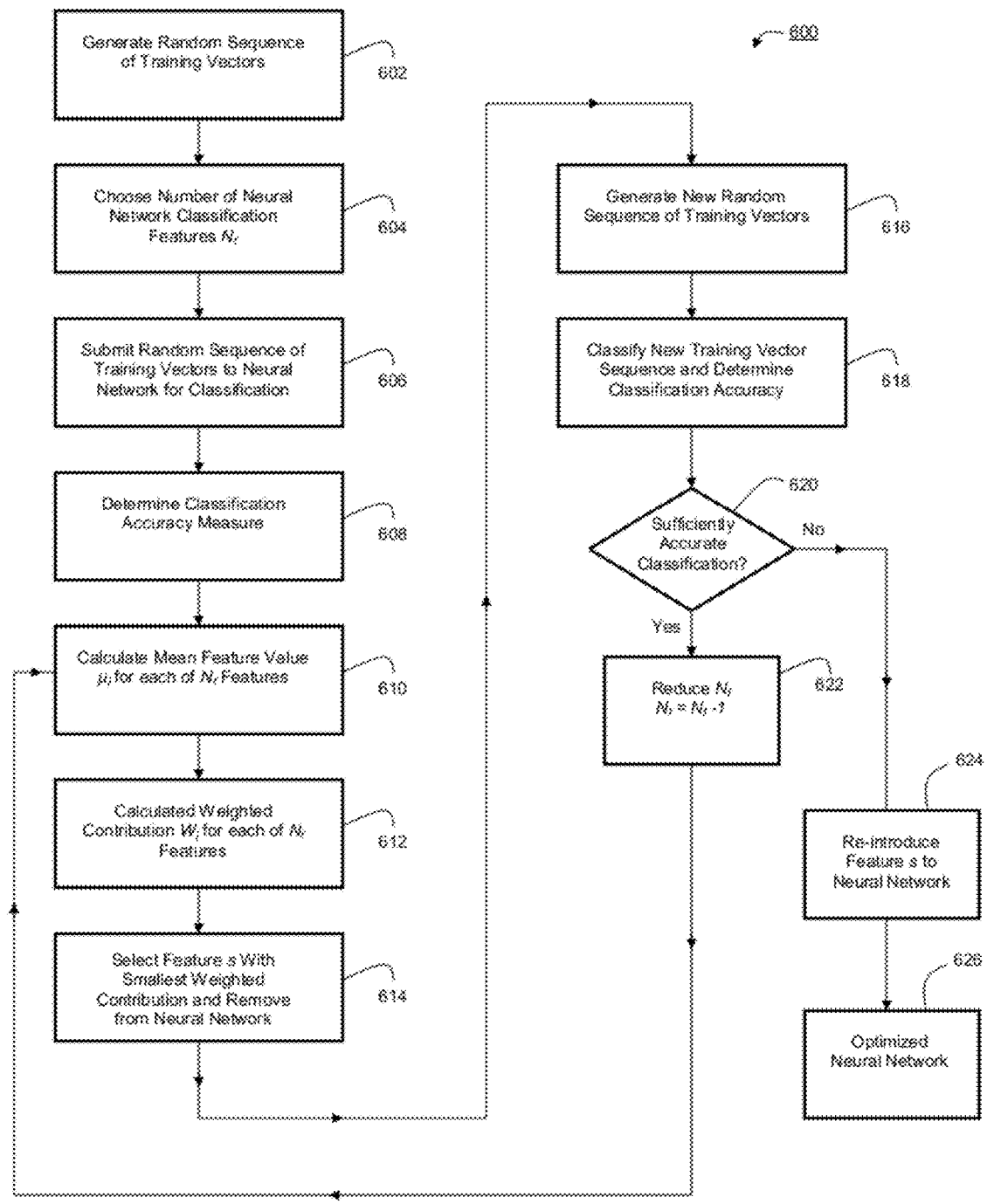
FIG. 6 is a flow chart showing steps involved in optimizing a trained neural network.

FIG. 6 is a flow chart 600 that includes an optional series of steps involved in optimizing a trained neural network. First step 602 includes generating a random sequence of training vectors to test the performance of the neural network. As before, the sequence of training vectors is constructed such that there exists an equal number of vectors corresponding to each of the $N_c$ classes identified previously.

Step 604 includes choosing the number of neural network classification features $N_f$. Initially, the value of $N_f$ typically consists of all the features that were calculated, for all image planes, which is the number of elements in the feature vector. Subsequent iterations of the optimization sequence can reduce the value of $N_f$ according to the classification performance of the neural network.

In step 606, the random sequence of vectors generated in step 602 is submitted to the neural network for classification. The classification of individual vectors is performed by the trained network in a manner consistent with the prior discussion. A feature vector is calculated for each ROI (e.g., based on one or more sub-sampled windows in the ROI), and the ROI is assigned to a particular class according to the known feature vectors for the various identified classes. In step 608, a classification accuracy score is determined either by visual inspection (e.g., by an operator) or by calculating the fraction of correct classification results.

In order to assess the relative significance of each of the $N_f$ features to the performance of the neural network, the mean feature value $\mu_j$ for each of the j classification features is calculated in step 610. Calculation of a mean feature value can be accomplished, for example, by calculating a mean value of the elements in a feature vector corresponding to a particular class. The elements in the feature vector can be weighted equally or differently in performing the calculation of $\mu_j$.

In a further step 612, the weighted contribution $W_j$ of each feature j of the $N_f$ total features under consideration by the neural network is calculated according to $$W_j = \sum_{k=1}^{N_f} \mu_j \gamma_k \quad (12)$$

where the $\gamma_k$ values are the node-to-node coupling constants within the neural network. Using Equation (12), the weighted contributions of each of the features (which generally correspond to classes) can be evaluated. In step 614, classification feature s having the smallest weighted contribution $W_s$ is identified as the "weakest" classification feature and removed from the set of classification features considered by the neural network.

In steps 616 and 618, a new random sequence of training vectors is generated according to the procedures discussed previously, and the training vectors are classified by the modified neural network, which now includes one less feature. A classification accuracy score is determined following classification of the vectors.

In logic step 620, the classification accuracy score is compared against a selected accuracy threshold. If the accuracy score is higher than the threshold, then the removed feature is deemed to be insignificant enough that it can be permanently removed from consideration by the neural network. The number of neural network classification features $N_f$ is reduced by one in step 622 and logical flow returns to step 610, where new mean feature values are calculated for the newly reduced set of classification features in the neural network. In some embodiments, before logical flow returns to step 610, the neural network can be retrained in order to adapt to the smaller number of features. This step is not necessary, but may be employed in some embodiments to improve the accuracy and/or speed of classification.

If the accuracy score is lower than the selected threshold, the removed feature is deemed to have been significant after all, and is re-introduced into the neural network in step 624. This completes the optimization of the network in step 626, and the network is then ready for use in classifying samples based on image sets.

If all features corresponding to a given input image plane are removed during the optimization process, that input plane is superfluous and need not be acquired in order to provide the classification signal. Further improvement in efficiency can be obtained by not acquiring such planes in future measurements, if the plane is not required for other purposes. The determination of which image planes are necessary can be made once, when devising a measurement protocol; or, it may be made and/or reviewed on an ongoing basis over time, in settings where factors such as sample variability may lead to changes in what image planes are necessary or helpful in making a classification.

Classification Using a Trained Neural Network

Figure 7:
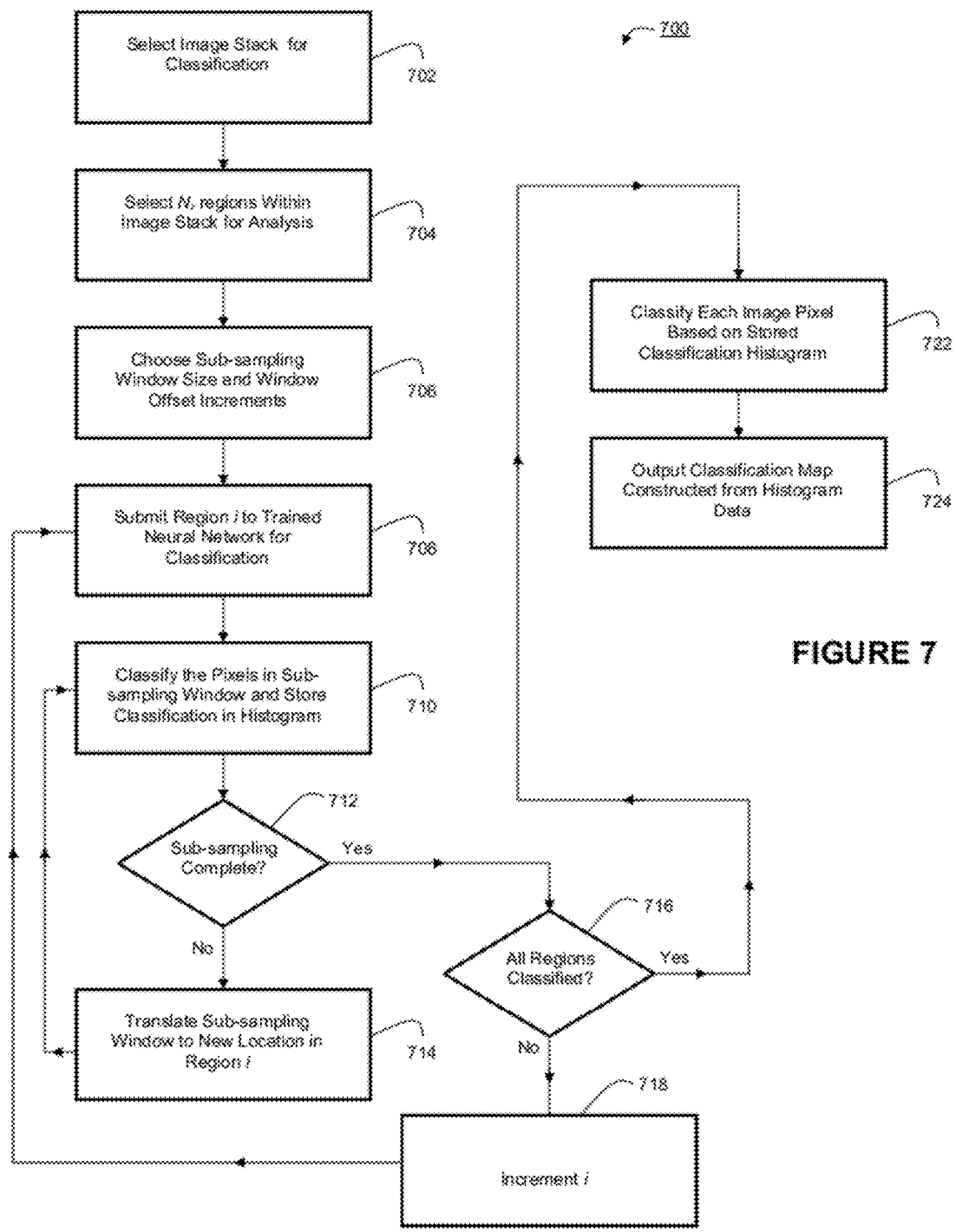
FIG. 7 is a flow chart showing steps involved in classifying a sample with a trained neural network.

The procedure by which a sample is classified according to its image stack is shown in FIG. 7. The figure includes a flow chart 700 that illustrates a series of steps in the classification procedure. In step 702, a particular image stack for the sample is chosen for classification, and in step 704, a number of regions $N_r$ within the image stack are selected for analysis. In some embodiments, the regions selected are subsets of the entire image. In other embodiments, the entire image can be selected for analysis.

The image stack being selected for analysis may include one or more images. The images in the image stack may include one or more raw spectral images, one or more composite images, and/or one or more unmixed images. For example, in certain embodiments, the image stack may include one composite image to provide spectral and spatial information and one gray scale image to provide spatial information. In other embodiments, for example, the image stack may include a set of unmixed images. Furthermore, in some embodiments, for example, the classification may be applied to only a single image containing only spatial (and no spectral) information. In any case, the neural network is trained in anticipation of the type of image stack being selected.

In step 706, a length l and width w of a sub-sampling window are selected. As discussed previously, the length and width of the sub-sampling window are typically chosen to be smaller than the mean length and width of each of the $N_r$ regions selected for analysis. In addition, step 706 includes selection of window offset increments $\Delta l$ and $\Delta w$. The offset increments are used to translate the sub-sampling window over the classification regions of the sample image in order to ensure that each of the pixels within the regions is classified at least once. In some embodiments, the values of $\Delta l$ and $\Delta w$ are both chosen to be smaller than and w, respectively, so that at least some pixels are classified multiple times since each translation of the sub-sampling window to a new position leaves a fraction of the previous window's pixels within the new window.

Figure 8:
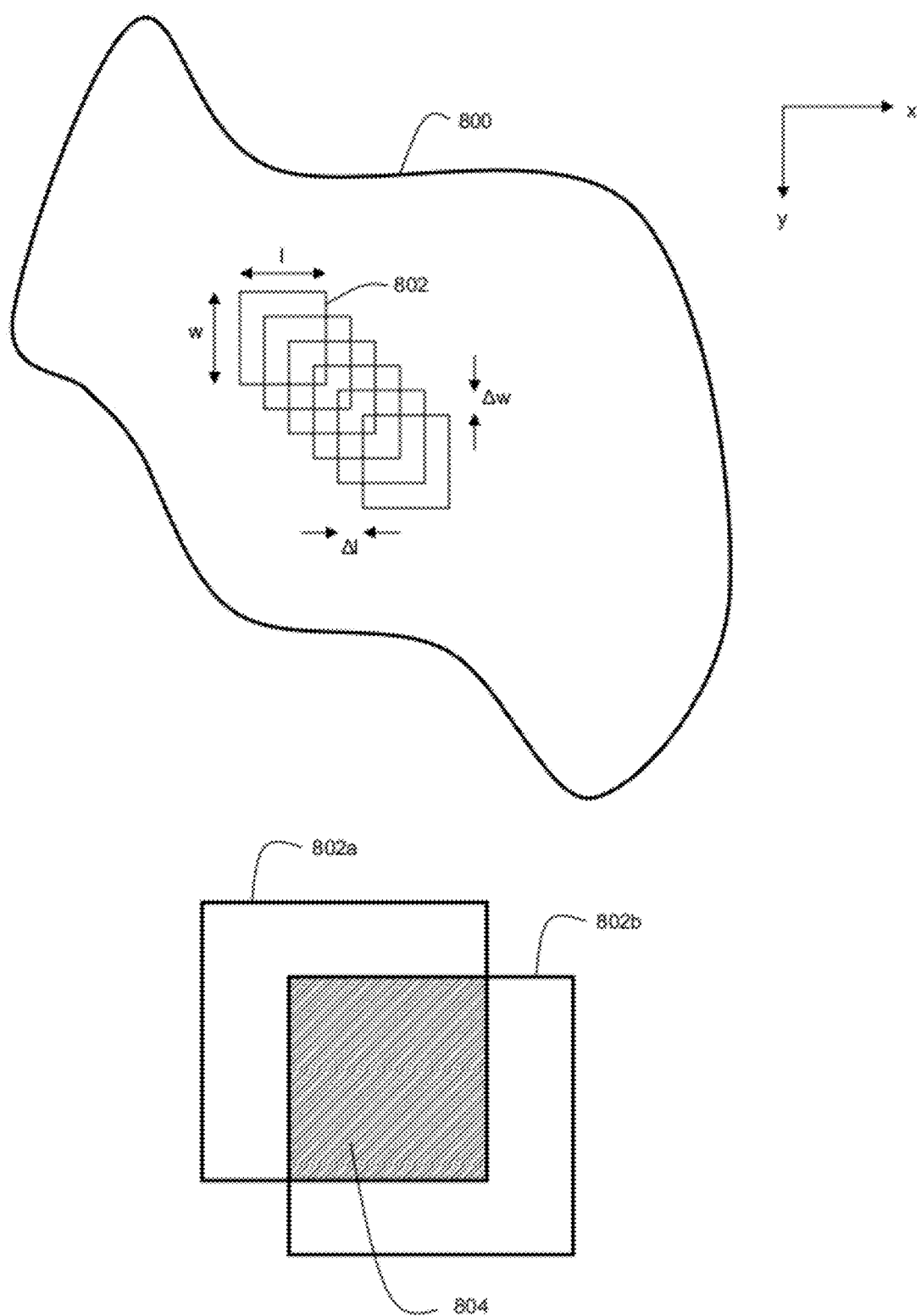
FIG. 8 is a schematic diagram showing a region of a sample images selected for classification.

In step 708, one of the regions selected in step 704 is submitted to the trained (and optionally, optimized) neural network for classification. The classification of the pixels in the windowed region is performed in step 710. The classification procedure is an iterative one, in which pixels within the selected region can be provisionally assigned a classification multiple times. The procedure begins by positioning sub-sampling window 802 within the selected region 800, as shown in FIG. 8. Sub-sampling window 802 has a length l in the x direction and a width w in they direction. The offset increments $\Delta l$ and $\Delta w$ are smaller than the length and width of the sub-sampling window, respectively.

In the first position of the sub-sampling window, each of the image pixels within the window is assigned a provisional classification based on the classification of the overall window region by the neural network using the methods discussed previously. The provisional pixel classifications can be stored within a pixel histogram for future reference. This corresponds to step 710. Referring again to FIG. 7, the next step is a logical decision 712 based on whether sub-sampling of the region is complete. If sub-sampling of the region is not complete, the sub-sampling window is then translated in the x and y directions by increments $\Delta l$ and $\Delta w$, respectively, as shown in step 714. The image pixels that fall within the new sub-sampling window position are then classified as before in step 710.

The procedure is illustrated schematically in the lower part of FIG. 8, in which window 802*a* represents the first position of the sub-sampling window and window 802*b* represents the second position of the window following translation. The classification of the pixels within the second window 802*b* by the neural network then proceeds as before. Note that the pixels that fall within shaded region 804 are classified a second time, since they are positioned within both windows 802*a* and 802*b*. The multiple classification of image pixels is a particular feature of certain embodiments of the methods disclosed herein.

Returning again to step 710 in FIG. 7, the classifications of individual pixels are again stored in the pixel histogram, and then the sub-sampling window is again translated and the classification procedure begins anew for a new window position. This iterative procedure, consisting of steps 710 through 714, can be specified to repeat for a selected number of window translations, such that a pixel classification histogram is built up.

Note that while FIG. 8 depicts the translation associated with step 714 as having both increments Δl and Δw, this is not necessary. For example, in some embodiments, the translation may scan horizontally, followed by a vertical translation when each horizontal scan across the selected region is complete, or vice versa. In certain embodiments, for example, each translation will correspond to a step of a single pixel and the translations across the region will generally result in each pixel being classified by number of pixels in the sampling window. Furthermore, in other embodiments, the translations need not be sequential. For example, the window translations can be systematic or random within the selected image region, although in some embodiments, an additional constraint that must be satisfied prior to termination of the classification procedure stipulates that all pixels within the selected region should be classified at least once, and preferably multiple times. Such a constraint is optional, however, and need not be imposed. Once the sub-sampling of the selected image region is complete, logical decision 716 determines a course of action based upon whether all of the selected regions of the sample image stack have been provisionally classified (e.g., a histogram of provisional classifications has been developed for every pixel in the selected regions of the selected image stack). If there are remaining unclassified regions, then counter i is incremented in step 718 (equivalent to selecting one of the unclassified regions) and classification of the selected regions begins at step 708 of flow chart 700.

Alternatively, if each of the regions of the sample image have been provisionally classified, then the initial classification procedure is finished and control passes to step 722, in which a final pixel classification step is performed based on the accumulated histogram data for each of the pixels. Due to the fact that pixels can be classified multiple times, entries in the classification histogram for particular pixels may not all be the same, and a pixel can be provisionally classified into more than one class.

A wide variety of algorithms can be used to establish a classification for a particular pixel from the histogram data. For example, the final classification of a given pixel can be the class to which the pixel was most frequently assigned. Alternatively, a more complex analysis of the statistical information in the histogram can be used to assign the final classification. For example, a pixel's classification can be established as the mean, median, or mode of the distribution of classifications for that pixel. Alternatively, more advanced statistical methods such as fuzzy logic or Bayesian logic can be applied to the histogram data to determine classifications for each of the image pixels.

In some embodiments, the histogram data can be used to "flag" particular regions of the sample according to classification. For example, if the histogram data for a particular pixel includes even a single instance in which the pixel was classified as belonging to a particular class, steps can be taken to ensure that the pixel is positively identified. Warning messages or sounds can be produced, or a sample image having the identified pixels highlighted for easy identification can be displayed. Flagging techniques can be particularly useful when tissue samples are examined for the presence of harmful agents or structures such as pathogens and cancer cells.

The final step 724 includes generating a classification map for the sample based on the final classification of step 722, or more generally, on the provisional pixel classification histogram data generated in the earlier steps. The classification map can include, for example, an image of the sample with classified regions highlighted in order to enhance contrast. The map can include, in some embodiments, multiple images of the sample, where each image only those portions of the sample that belong to a particular class, as identified by the neural network. The classification map can also include numerical data specifying classified sample regions, and statistical information such as the distribution and relative abundance of various classes within the sample. This information is particularly useful when the classified regions correspond to different structural, chemical, or biological entities within the sample. The classification image map can be displayed on display device 118, for example, and can be stored in electronic form on a storage medium by electronic control system 114. Generation of the classification map completes the classification procedure, and generally yields accurate class data for a wide variety of samples.

Other features and aspects of the classification methods and systems discussed herein are disclosed, for example, in U.S. Pat. No. 7,555,155 entitled "CLASSIFYING IMAGE FEATURES," the entire contents of which are incorporated herein by reference.

Multi-Component Staining with a Common Stain

Because the techniques described above combine spectral unmixing techniques with further classification techniques based on, for example, signal strength, shape, spectral features, and textural features, they can be used to label M components (or "targets") of a sample with N<M stains, so that at least two components are labeled with a common stain. The commonly stained components can be distinguished from one another based, at least in part, on the further classification techniques, so that different parts of the sample can be classified into M>N respective classes using only N stains.

For biological samples, this provides a practical and relatively easy method to increase the number of immunohistochemical (or immunofluorescence targets) beyond two, using conventional double labeling strategies, such as those that rely on rabbit-mouse antibody combinations and quantum-dots conjugated to antibodies through streptavidin-biotin binding. For example, the rabbit and mouse antibodies can each be combined with a common stain to provide the respective probes for the targets to be labeled. So, while each labeled target requires a separate probe, the probes can include a common stain, which can simplify sample preparation and improve data acquisition. Specifically, in certain embodiments, an imaging system having sufficient resolution to resolve the cell compartments in a sample is used with image analysis software, such as that those disclosed herein, to segment the cell compartments, so that different components in a specific cell compartment can be spectrally resolved, even though a common stain is used on multiple targets in different compartments.

In some embodiments, sample preparation can be simplified because the number of targets that can be labeled with commercially available probes can be increased. That is, probes that label different targets, but which have a common stain, can be used on the same sample. Furthermore, data acquisition can be improved because the light emitted by the sample can be separated into fewer spectral channels (because there are fewer stains to distinguish), thereby increasing signal-to-noise ratio and detection efficiency. For example, in certain embodiments, a simple RGB camera can be used to the collect the spectral images (e.g., so that light emitted by the sample is separated into three spectral channels).

In some embodiments, for example, each cell is split into two compartments, nuclear and non-nuclear, which includes cytoplasm and membrane. Even though a common stain (e.g., a chromogen or fluorophore) might end up in both compartments, its presence indicates different things depending on which compartment it is in. A representative system includes quantum dots combined with a nuclear counterstain such as DAPI. DAPI provides a bright and specific staining of nuclei, which supports robust cellular detection and compartment segmentation. Once cellular compartments have been determined, a signal can be assigned accordingly. For example, four receptors, ER, PR, Her1 and Her2, such as those used in breast cancer research and diagnosis, can be detected with two quantum-dot-based detection systems, such a 585 nm and a 655 nm quantum dot.

The approach can be combined with the spectral unmixing and classification techniques described herein to resolve the spectrally and spatially overlapping signals.

Optical System Components

System 100 can include a wide variety of optical elements and devices for capturing images of a sample that are used in subsequent classification algorithms. Light source 102 can be an incoherent light source such as an incandescent lamp, a fluorescent lamp, or a diode. Light source 102 can also be a coherent source such as a laser source, and the coherent source can provide continuous wave (CW) or pulsed light. Light source 102 may contain multiple light source elements for producing light having a range of wavelengths (e.g., multiple diodes). When the light produced by light source 102 is pulsed (i.e., time-gated), various properties of the light pulses can be manipulated according to control signals provided to light source 102 from electronic control system 114 via communication line 132. Light source 102 can also include various optical elements such as lenses, mirrors, waveplates, and nonlinear crystals, all of which can be used to produce light having selected characteristics. In general, light source 102 includes optical elements and devices configured to provide light having desired spectral, spatial, and, in some embodiments, temporal properties.

Light conditioning optics 104 and light collecting optics 110 can include a variety of optical elements for manipulating the properties of light incident on, and emitted from, a sample of interest. For example, light conditioning optics 104 and light collecting optics 110 can each include spectral filter elements for selecting particular wavelength bands from incident and emitted light. The spectral filter elements can include, for example, interference filters mounted on a filter. In some embodiments, adjustable filter elements based on liquid crystal masks can be used to change the spectral properties of the incident or emitted light. Liquid crystal based devices can be controlled by electronic control system 114 via communication lines 134 and 138.

Light conditioning optics 104 and light collecting optics 110 can also include elements such as spatial light masks, spatial light modulators, and optical pulse shapers in order to manipulate the spatial distribution of light incident on, or emitted from, a sample. Spatial light modulators and other adaptive devices can also be controlled via communication lines 134 and 138 by electronic control system 114.

Finally, light conditioning optics 104 and light collecting optics 110 can include other common optical elements such as mirrors, lenses, beamsplitters, waveplates, and the like, configured in order to impart selected characteristics to the incident or emitted light.

In general, detector 112 includes one or more measurement devices configured to detect and capture light emitted by a sample as multiple images of the sample. Detector 112 can include devices such as CCD arrays and photomultiplier tubes, along with their respective control systems, for acquiring the images. The adaptive optical devices in detector 112 can, in general, be controlled by electronic control system 114 via communication line 130.

Software

The steps described above in connection with various methods for collecting, processing, analyzing, interpreting, and displaying information from samples can be implemented in computer programs using standard programming techniques. Such programs are designed to execute on programmable computers or specifically designed integrated circuits, each comprising an electronic processor, a data storage system (including memory and/or storage elements), at least one input device, and least one output device, such as a display or printer. The program code is applied to input data (e.g., images from the detector) to perform the functions described herein and generate output information (e.g., images showing classified regions of samples, statistical information about sample components, etc.), which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis and control functions described herein.

EXAMPLES

The following examples are intended to be exemplary of the systems and methods disclosed herein, but should not in any way be construed as limiting the scope of the subsequent claims.

Figure 10A:
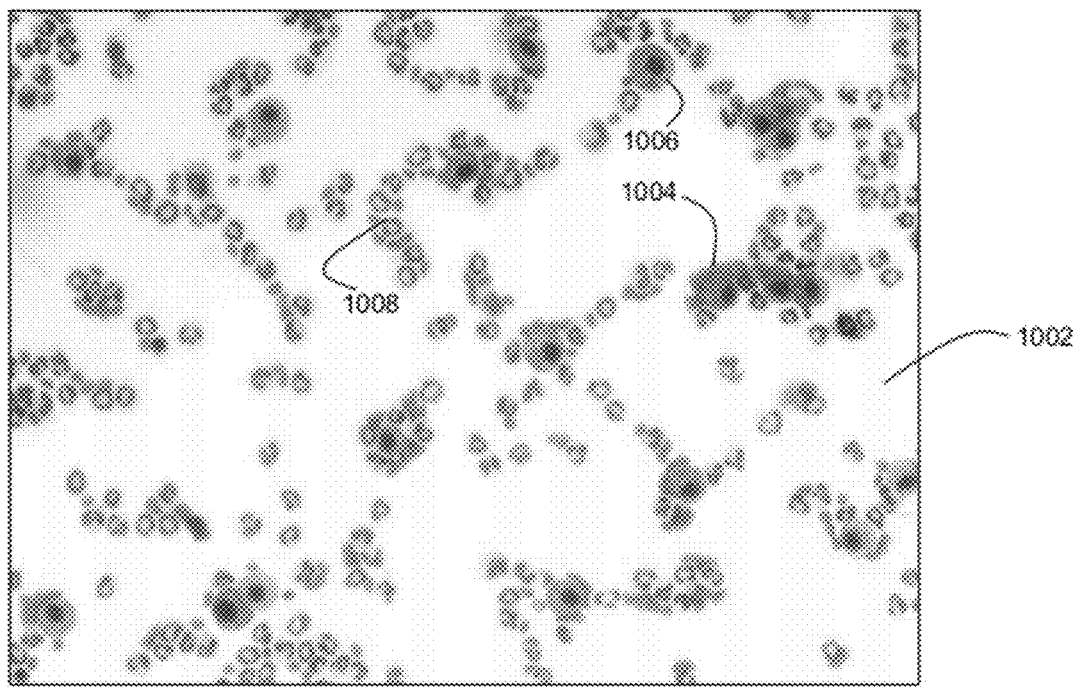
FIGS. 10A-10I show an example of a classification technique disclosed herein being applied to data for a real sample.

FIG. 10A shows an example of a sample of rat blood that is classified according to some of the methods of the present disclosure. The blood sample includes 4 classes: background 1002, red cells 1004, monocytes 1006, and polymorphonuclear neutrophils (PMNs) 1008. A set of spectral images corresponding to incident light transmitted through the sample were collected and then transformed from measured intensities to optical densities (ODs). The resulting transformed images formed a spectral cube of image data.

Figure 10B:
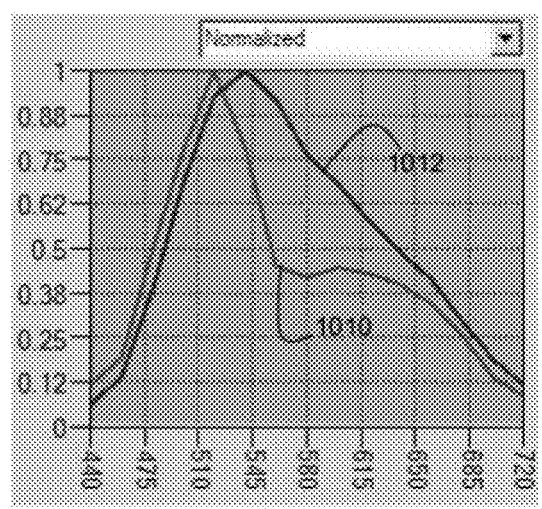
Figure 10C:
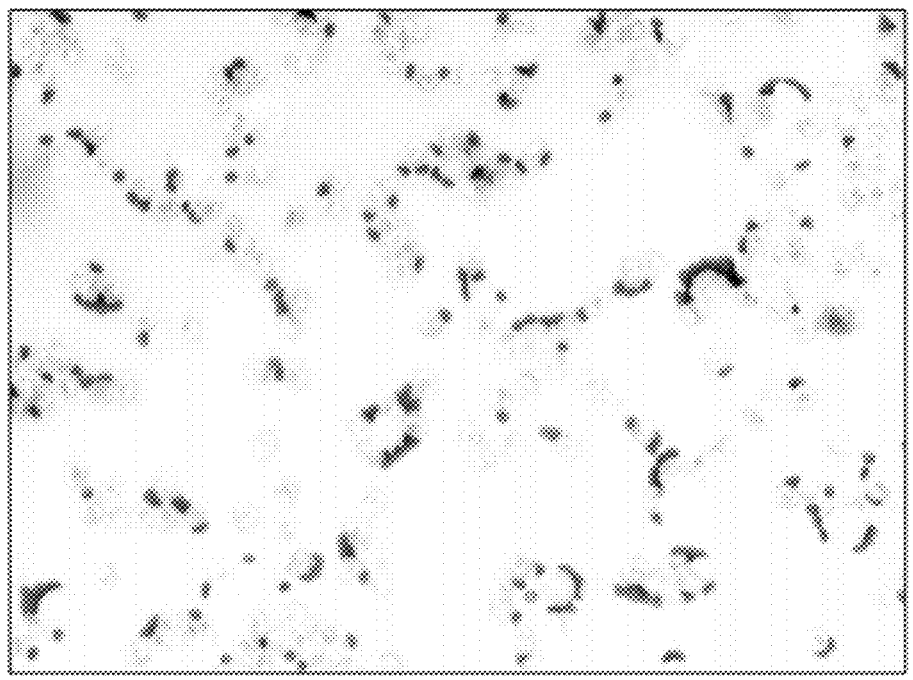
Figure 10D:
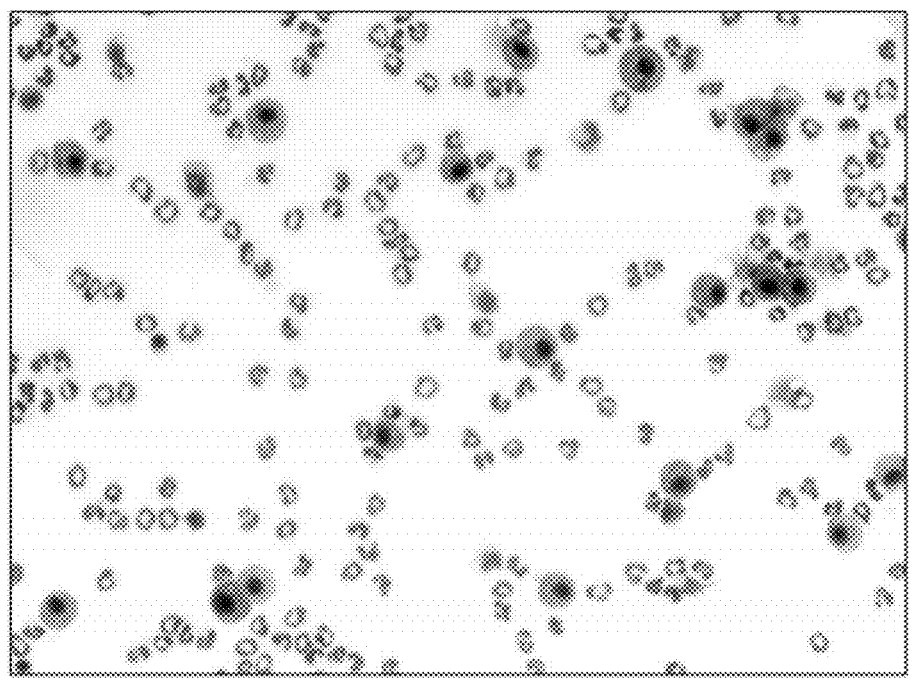

The spectral image cube was unmixed into separate images corresponding to a red component 1010 and a blue component 1012 of the blood sample, as shown in FIG. 10B. FIG. 10C and FIG. 10D show the results of this spectral unmixing operation. FIG. 10C shows an example of an unmixed image corresponding to the red component 1010 and FIG. 10D shows an example of an unmixed image corresponding to the blue component 1012.

Figure 10E:
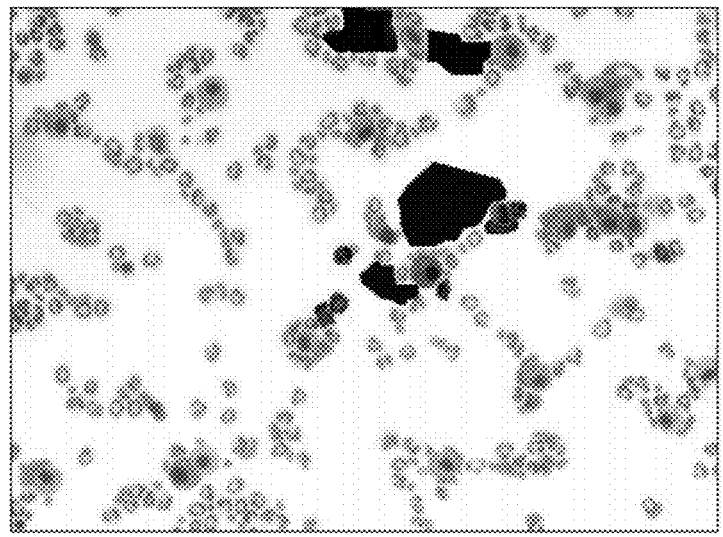
Figure 10F:
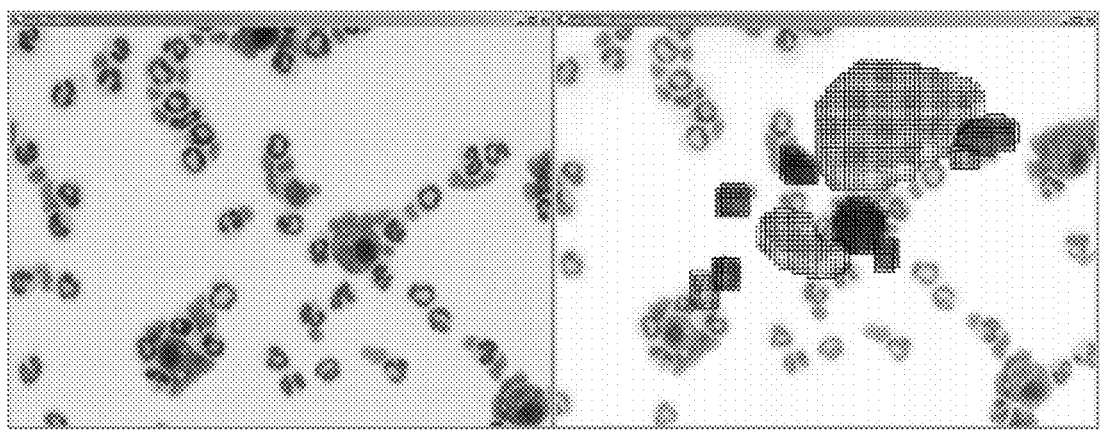

Following the unmixing step, a composite plane was generated by a linear ramp function used as the weighting function, so that the unmixed planes and composite plane formed a 3-plane stack. Next, training regions were selected on the image stack, and a neural network-based classifier was trained according to the selected regions. FIG. 10E shows selected training regions superimposed on an image of the sample. Training of the neural network includes calculation of features related to the identified training regions. An expanded view of this process for the training regions is shown in FIG. 10F. The left side of FIG. 10F shows a view of an expanded region of a sample image that includes selected training regions. On the right side of FIG. 10F, the selected training regions have been sub-sampled, and the sub-sampling windows are superimposed over the regions.

Figure 10G:
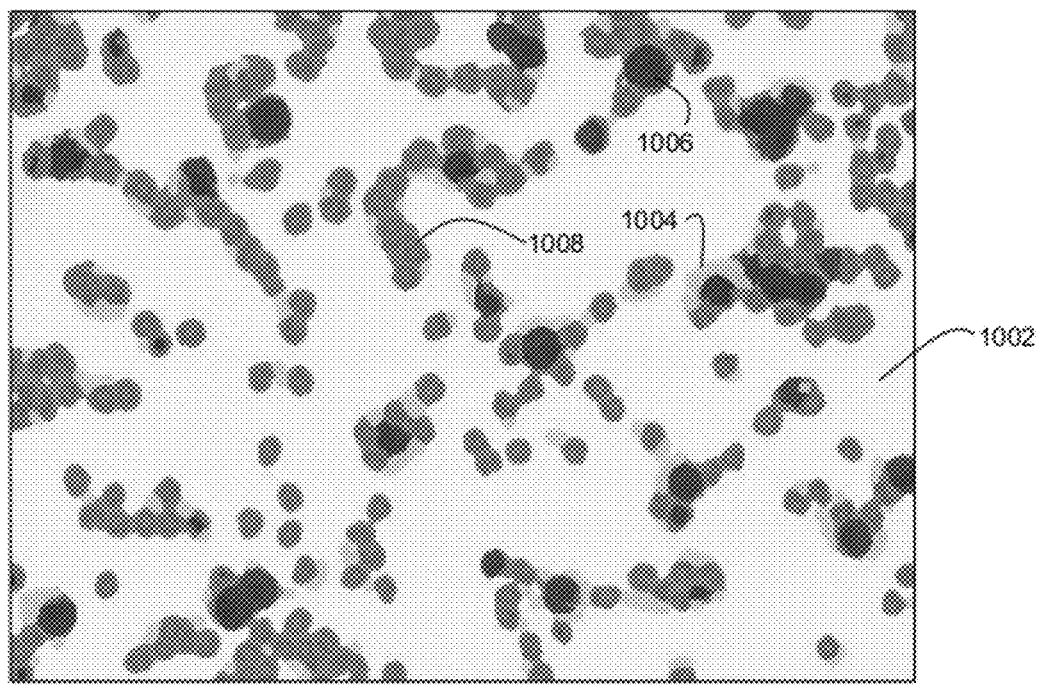

The trained neural network-based classifier was then used to classify the remaining regions of the images. The results are shown in FIG. 10G. The image features corresponding to the background class 1002, red cell class 1004, monocyte class 1006, and PMN class 1008 are all accurately determined and identified using the neural network-based classifier.

Figure 10H:
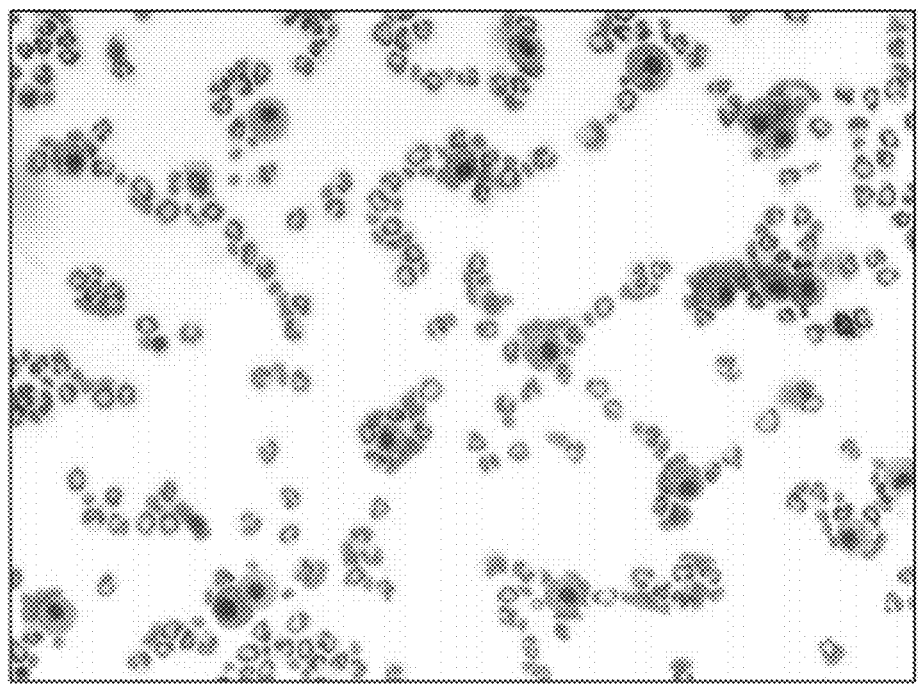
Figure 10I:
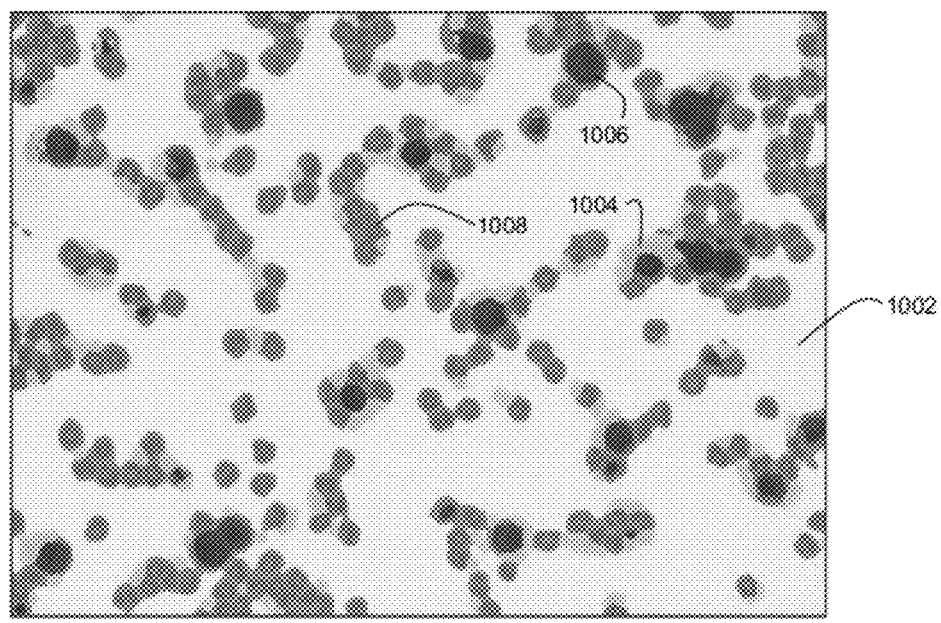

In another example, a 3-plane RGB image was generated from the same image cube of spectral images, and selected regions of the RGB image were used to train and optimize a neural network. This RGB image was generated by summing all the spectral bands in the blue to form a blue plane, summing all the spectral bands in the green to form a green plane, and summing all the spectral bands in the red to form a red plane. The result mimics what would have resulted if the scene were imaged using a conventional RGB camera. The trained and optimized neural network was then used to classify the remainder of the composite image. FIG. 10H shows the RGB image, and FIG. 10I shows the results of the classification operations carried out. The image features corresponding to the background class 1002, red cell class 1004, monocyte class 1006, and PMN class 1008 are all accurately determined and identified using the neural network-based classifier. The automated methods disclosed herein provide an effective means for classifying the blood sample.

Figure 12:
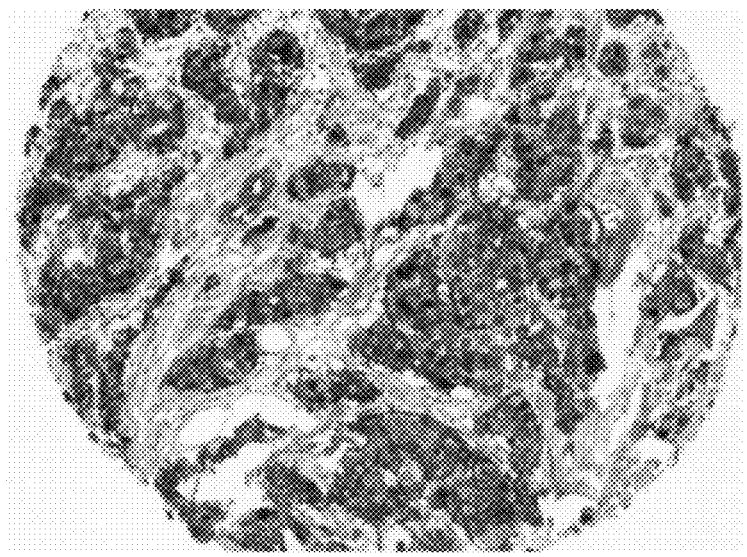
FIG. 12 is an image of a sample labeled with multiple antibody probes.

As an example of multi-component staining with common stains, FIG. 12 shows a red-green-blue (RGB) image of a tissue sample. To investigate expression of ER, PR, and Her2 proteins in the sample, the sample in FIG. 12 was labeled with antibody probes for each of these proteins. The ER probe included DAB as a chromogen bound to the ER-specific antibody. The PR and Her2 probes included Vector Red bound to PR- and Her2-specific antibodies. The sample was treated with each of these probes. As a result of this staining protocol, both PR and Her2 proteins were stained with Vector Red, while ER was separately stained with DAB. However, because certain stains are specific to certain cell components (e.g., in this case, DAB is specific to nuclei and helps to demarcate nuclear and non-nuclear cellular compartments in the sample), signals due to different proteins can be effectively separated even though they arise from the same chromogen—that is, even though more than one sample component is labeled with the same chromogen.

Figure 13A:
FIGS. 13A-C are unmixed component images obtained from the image FIG. 12.
Figure 13B:
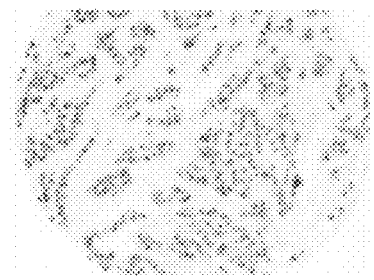
Figure 13C:
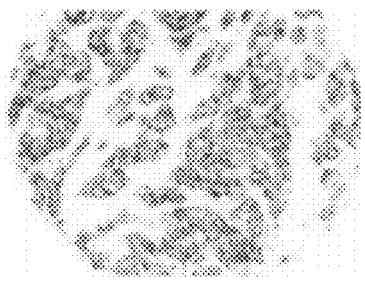

FIGS. 13A-C show the results of spectral unmixing of the image shown in FIG. 12. FIG. 13A shows an image that corresponds to contributions from substantially only hematoxylin (e.g., the counterstain) to the image shown in FIG. 12. The image in FIG. 13B corresponds to contributions from substantially only DAB in the image of FIG. 12, and the image in FIG. 13C corresponds to contributions from substantially only Vector Red in the image of FIG. 12. The image in FIG. 13B is indicative of expression of ER in the tissue sample, while the image in FIG. 13C is indicative of expression of PR and Her2 in the tissue sample. Individual contributions from only PR and only Her2 can be subsequently obtained from the image in FIG. 13C by using information derived from FIG. 13A and FIG. 13B to separate individual cells in the sample into different compartments (e.g., nuclear compartments and non-nuclear compartments). For example, since PR is expressed in nuclear compartments and Her2 is expressed in non-nuclear compartments (e.g., some cellular membranes) in the sample of FIG. 12, contributions from Vector Red in nuclear compartments can be attributed to expression of PR, and contributions from Vector Red in non-nuclear compartments can be attributed to expression of Her2. Contributions from DAB in nuclear compartments can be attributed to expression of ER, since ER-based antibody probes are the only ones that include DAB as a stain in the sample of FIG. 12.

Based on the unmixed images, different regions of sample images can be classified into one or more different classes according to levels of expression of different molecules such as proteins in the sample. FIGS. 14A-D show four different tissue sections in which different portions of the tissue section in each figure are assigned to different classes according to expression of various proteins in the sample. Expression levels of the various proteins were determined from unmixed images for each sample, where different unmixed images for each sample corresponded to different protein-specific probes.

Figures 15A, 15B:
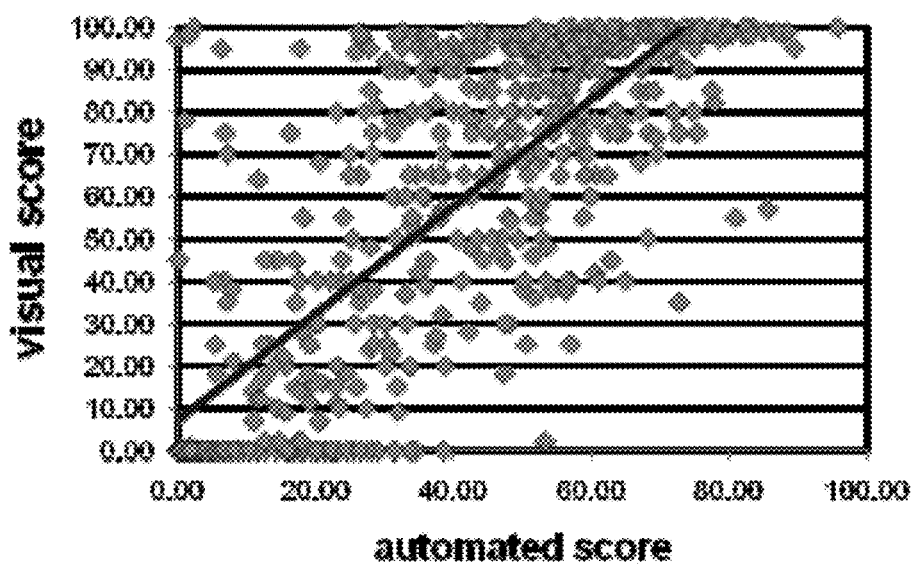
FIG. 15A is a plot showing a correlation between automated and visual inspection scores for ER expression in samples.
FIG. 15B is a chart showing a correlation between automated and visual inspection scores for Her2 expression in samples.

Following classification of the various regions of the samples shown in FIGS. 14A-D, the automated classification results were compared with results from visual inspection of the samples by trained technicians. FIG. 15A shows the correlation between automated and visual inspection scores for ER expression, with a correlation coefficient of $R=0.8$. FIG. 15B shows a comparison between automated and visual inspection scores for Her2 expression; the correlation coefficient was $R=0.85$. These correlations indicate that machine-based classification provides classification results that agree well with results from human operators.

Figure 16:
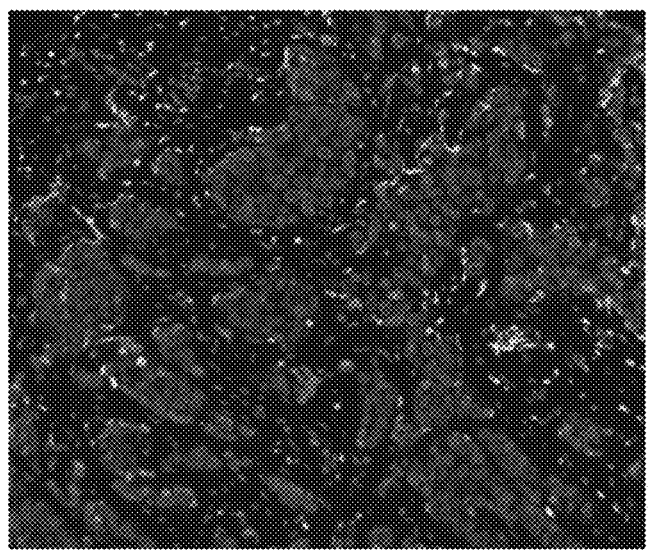
FIG. 16 is an image of a sample labeled with antibody-based probes that include quantum dot-based fluorophores.

FIG. 16 shows an image of another sample that is labeled with probes that target ER, Her1, and Her2 expression. In this sample, the stains bound to the ER-, Her1-, and Her2-specific antibodies are quantum dot-based fluorophores. More particularly, the ER-specific probe includes a quantum dot-based fluorophore that emits at 655 nm, the Her1-specific probe includes a quantum dot-based fluorophore that emits at 585 nm, and the Her2-specific probe includes a quantum dot-based fluorophore that emits at 655 nm. The spectral image in FIG. 16 includes contributions from each of the above quantum dot fluorophores. As in the example shown in FIGS. 13A-C, the quantum dot-based fluorophore is used to label both ER and Her2 in the sample.

Figure 17A:
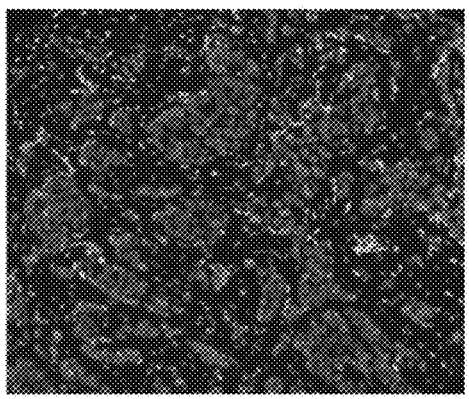
FIG. 17A is an unmixed component image that corresponds to a counterstain applied to the sample of FIG. 16.
Figure 17B:
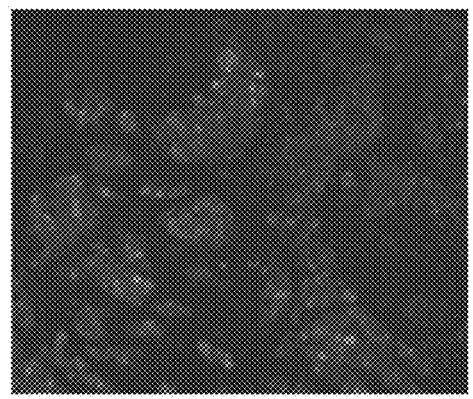
FIGS. 17B and 17C are unmixed component images that correspond to antibody-based probes used to label the sample of FIG. 16, and include quantum dot-based fluorophores that emit at 655 nm and 585 nm, respectively.
Figure 17C:
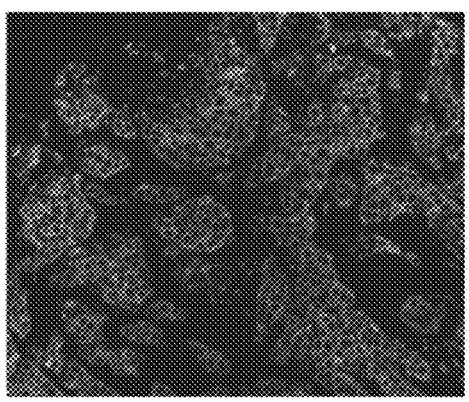
Figure 17D:
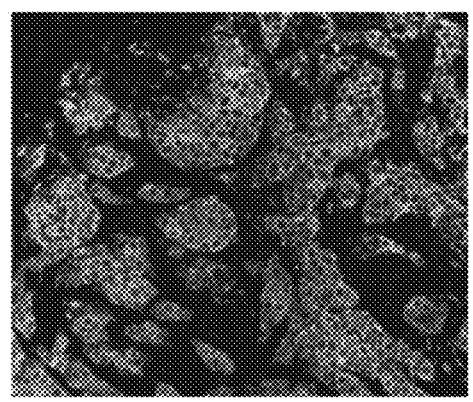
FIG. 17D is a composite image formed from the combination of the images in FIGS. 17A-C.

The image in FIG. 16 can be unmixed to obtain component images corresponding substantially only to contributions from each of the different labeled components in the sample. With respect to FIG. 16, the image was unmixed to obtain in FIG. 17A a component image corresponding to the DAPI counterstain applied to the sample in FIG. 16. The unmixed component image in FIG. 17B corresponds to 655 nm fluorescence emission from both ER and Her2 in the sample. FIG. 17C is an unmixed component image that shows 585 nm fluorescence emission corresponding Her1 in the sample. The various component images in FIGS. 17A-C are combined in FIG. 17D to form a composite image that includes contributions corresponding to DAPI, ER, Her1, and Her2 in the sample, and omitting background contributions that arise from autofluorescence, for example. By using spatial information about sample compartments (e.g., cellular compartments) derived from the images, the expression of ER and Her2 in the sample can be separately identified from FIG. 17B. Subsequently, the images in FIGS. 17A-C are used to classify different regions of the sample using machine-based classification algorithms as discussed above.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus comprising:
   a means for obtaining a set of spectral images of a sample, wherein the sample has M>2 different components labeled with N<M stains so that at least two different components are labeled with a common stain and wherein the sample is further stained with at least one histological stain;
   a display device; and
   an electronic processor connected to the means for obtaining the set of spectral images and the display device, and comprising software instructions that, when executed, cause the electronic processor to:
   display at least one image of the set of spectral images on the display device, wherein the at least one image shows the at least two different components labeled with the common stain;
   analyze an image stack derived from the set of spectral images to generate a first image comprising contributions from only the at least one histological stain, and a second image comprising contributions from the at least two different components labeled with the common stain;
   classify different cellular compartments of the sample into respective classes based on one or more of signal strength, shape, spectral features, and textural features in at least the first image;
   identify each of the at least two different components in the sample labeled with the common stain based on the classified cellular compartments of the sample;
   generate output image information from the set of spectral images based on the classified cellular compartments and comprising a set of additional images, wherein each additional image in the set shows a different one of the at least two different components labeled with the common stain; and
   display the output image information on the display device.

2. The apparatus of claim 1, wherein the electronic processor further comprises software instructions that, when executed, cause the electronic processor to determine relative amounts of multiple ones of the M different components in different regions of the sample.

3. The apparatus of claim 1, wherein the electronic processor is configured to perform the classification by decomposing the set of spectral images into an unmixed image set, wherein each member of the unmixed image set corresponds to a respective one of the stains, and to classify the different parts of the sample into the respective classes based on an image stack comprising one or more of the unmixed images.

4. The apparatus of claim 1, wherein M>2 and N>1.

5. The apparatus of claim 1, wherein the means for obtaining the set of spectral images comprises an RGB camera.

6. The apparatus of claim 2, wherein the electronic processor further comprises software instructions that, when executed, cause the electronic processor to perform the determination based on the set of spectral images and the classification.

7. The apparatus of claim 1, wherein the electronic processor further comprises software instructions that, when executed, cause the electronic processor to:
   decompose the set of spectral images into an unmixed image set, each member of the unmixed image set corresponding to a spectral contribution from a respective one of the N stains for labeling the M types of components or the histological stain; and
   determine relative amounts of multiple ones of the M different components in different regions of the sample based on the unmixed image set.

8. The apparatus of claim 1, wherein the electronic processor comprises software instructions that, when executed, cause the electronic processor to classify the different cellular compartments of the sample into respective classes using a neural network-based classifier.

* * * * *